United States Patent [19]
Willis

[11] Patent Number: 5,962,016
[45] Date of Patent: Oct. 5, 1999

[54] MULTIVESICULAR LIPOSOMES UTILIZING NEUTRAL LIPIDS TO MODIFY IN VIVO RELEASE

[75] Inventor: Randall C. Willis, Solana Beach, Calif.

[73] Assignee: DepoTech Corporation, San Diego, Calif.

[21] Appl. No.: 08/974,296

[22] Filed: Nov. 19, 1997

Related U.S. Application Data

[62] Division of application No. 08/792,566, Jan. 31, 1997.

[51] Int. Cl.$^6$ .................................................. A61K 9/133
[52] U.S. Cl. .......................................................... 424/450
[58] Field of Search .................................. 424/450, 1.21, 424/9.321, 9.51, 417; 264/4.1, 4.3; 436/829; 428/402.2; 935/52

[56] References Cited

U.S. PATENT DOCUMENTS 5,422,120  6/1995  Kim .......................................... 424/450

OTHER PUBLICATIONS

Hamilton et al., "Solubilization and localization of triolein in phosphatidylcholine bilayers: A $^{13}$C NMR study", *Proc. Natl. Acad. Sci. USA*, vol. 78, No. 11, pp. 6878–6882 (Nov. 1981).

Spooner, et al. "Effect of Free Cholesterol on Incorporation of Triolein in Phospholipid Bilayer", *Biochemistry*, 26:5820–5825 (1987).

*Primary Examiner*—Gollamudi S. Kishore
*Attorney, Agent, or Firm*—Fish & Richardson P.C.

[57] ABSTRACT

The rate of release of encapsulated active compound from a multivesicular liposomal (MVL) formulation is modified by selection of a neutral lipid component. A family of MVL formulations containing different slow:fast release neutral lipid molar ratios display different release rates depending upon the molar ratio of the fast release neutral lipid to the slow release neutral lipid in each member. Incubation in plasma or a plasma-like medium at in vivo temperatures so as to obtain a release rate curve for each allows selection from among the members of the family of a liposomal formulation with a desired rate of release in vivo.

6 Claims, 12 Drawing Sheets

MULTIVESICULAR LIPOSOMES UTILIZING NEUTRAL LIPIDS TO MODIFY IN VIVO RELEASE

This application is a divisional of U.S. patent application Ser. No. 792,566, filed Jan. 31, 1997 (pending).

BACKGROUND OF THE INVENTION

This invention relates to liposomal formulations of compounds such as drugs. More particularly this invention relates to methods of modifying the in vivo rate of release of encapsulated compounds from multivesicular liposomes by the choice of the neutral lipid in the liposomal formulation.

When phospholipids and many other amphipathic lipids are dispersed gently in an aqueous medium they swell, hydrate, and spontaneously form multilamellar concentric bilayer vesicles with layers of aqueous media separating the lipid bilayers. These systems are commonly referred to as multilamellar liposomes or multilamellar vesicles (MLV), and usually have diameters of from 0.2 to 5 $\mu$m. Sonication of MLV results in the formation of small unilamellar vesicles (SUV) bounded by a single lipid bilayer with diameters usually in the range of from 20 to 100 nm, containing an aqueous solution. Multivesicular liposomes (MVL) differ from MLV and SUV in the way they are manufactured, in the random, non-concentric arrangement of aqueous-containing chambers within the liposome, and in the inclusion of neutral lipids necessary to form the MVL.

Various types of lipids differing in chain length, saturation, and head group have been used in liposomal drug formulations for years, including the unilamellar, multilamellar, and multivesicular liposomes mentioned above. The neutral lipids used in the manufacture of multivesicular liposomes to date have been primarily limited to triolein and tricaprylin.

One of the major goals of the field is to develop liposomal formulations for controlled in vivo release of drugs and other active agents of interest. Certain drugs need to be released fairly rapidly upon emplacement of the liposomal depot, and others require a relatively slow rate of release over a sustained period of time. Heretofore, the rate of release of a biologically active compound from a liposomal formulation has been modified by selection of the amphipathic lipid, the accepted membrane forming lipid, or by manipulation of the phospholipid/cholesterol molar ratio. Alternatively, such compounds as an acid or an osmolality spacer have been included in the aqueous solution for encapsulation to aid in modifying the rate of release of the encapsulated biologically active compound.

The control of release rates from liposomal formulations is complicated by the fact that many biologically active agents, such as proteins, need to be stored at reduced temperatures, i.e., about 4° C., to retain full activity. Unfortunately, some liposomal formulations that display excellent release rates at in vivo temperatures disintegrate rather rapidly at such storage temperatures.

Thus, the need exists for more and better methods for selecting liposomal formulations that maximize control over the rate of release of the encapsulated active compound while simultaneously affording shelf life stability for long periods of time at storage temperatures of about 4° C., for example 2 to 10° C.

SUMMARY OF THE INVENTION

In general, the invention features a method for modifying the rate of release of a biologically active compound, such as a drug, that is encapsulated in a multivesicular liposomal formulation by utilizing in the formulation a neutral lipid component having a selected molar ratio of a slow release neutral lipid to a fast release neutral lipid, wherein the proportion of the fast release neutral lipid in the molar ratio is increased to increase the rate of release of the biologically active compound. Alternatively, the proportion of the slow release neutral lipid in the molar ratio can be increased to decrease the rate of release of the biologically active compound. Generally, the slow:fast neutral lipid molar ratio is in the range from about 1:1 to 0:1, for example 1:4 to 1:100, or 1:4 to 1:27, and the molar ratio of the neutral lipid component to the total lipid component (all the lipids in the liposome) is in the range from about 0.01 to about 0.21.

For modifying the in vivo release rate, the melting point of the neutral lipid component preferably is at or below the in vivo temperature at which the formulation is to be used, as well as at or below the temperature at which the formulation is to be stored.

Slow release neutral lipids useful in the new method of this invention are, for example, triolein, tripalmitolein, trimyristolein, trilaurin, and tricaprin with triolein being most preferred. Useful fast release neutral lipids include, e.g., tricaprylin and tricaproin, and mixtures thereof. However, tricaproin and other similar lipids are usually not used as the sole neutral lipid in a formulation of multivesicular liposomes intended for use in vivo.

In another embodiment, the present invention provides a liposomal composition comprising a therapeutically effective amount of a biologically active compound encapsulated in a multivesicular liposome formulation wherein the formulation comprises a neutral lipid component comprising a molar ratio of slow release neutral lipid to fast release neutral lipid from about 1:1 to 1:100, for example from about 1:3 to 1:54, 1:4 to 1:27, or from about 1:4 to 1:18.

In yet another embodiment, the invention features a method for selecting a multivesicular liposomal formulation for encapsulating a selected biologically active compound so as to obtain a desired release rate profile of the active compound in vitro and/or a desired therapeutic release rate in vivo. In this embodiment of the invention, a family of MVL formulations that encapsulate the selected biologically active compound is prepared wherein each member of the family utilizes a neutral lipid component having a different slow:fast neutral lipid molar ratio, generally in the range from 1:0 to 0:1. For example, a family of formulations utilizing slow:fast neutral lipid molar ratios of 1:0, 1:1, 1:4, 1:18, 1:27, 1:100, 0:1 can be prepared. Each member of the family of formulations is incubated in the medium in which the desired rate of release is to be obtained, i.e., either in a storage medium at storage temperature or in human plasma, a plasma-like medium, or in a physiological medium into which the physiologically active substance is to be released, such as cerebrospinal fluid (CSF) at body temperature. By this means a release rate profile is obtained for each formulation. Then the formulation having the slow:fast neutral lipid ratio that yields the desired release rate profile under the desired conditions for the selected biologically active substance is selected.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The practice of this invention provides the advantage that a formulation of multivesicular liposomes can be selected to have relatively rapid release in vivo that does not compromise the desire of slow release at storage conditions. The method of the invention, therefore, provides a rationale for obtaining a desired release rate through selection of the neutral lipid component used in manufacture of the MVL without compromising the desire for the formulation to have a slow release at storage conditions. Further, the control over the rate of release under in vivo conditions operates more or less independently of the composition of the aqueous phase encapsulated or the combination of the other lipids in the formulations.

This finding is particular to multivesicular liposomes since other types of liposomes do not contain neutral lipids in the lipid component and/or do not incorporate the neutral lipids into closely packed, non-concentric vesicles.

Other features and advantages of the invention will be apparent from the following detailed description, and from the claims.

triolein only; (Δ) 1:4 triolein:tricaproin; (∇) 1:9 triolein:tricaproin; (◇) 1:18 triolein:tricaproin; and (+) tricaproin only.

Figure 15:
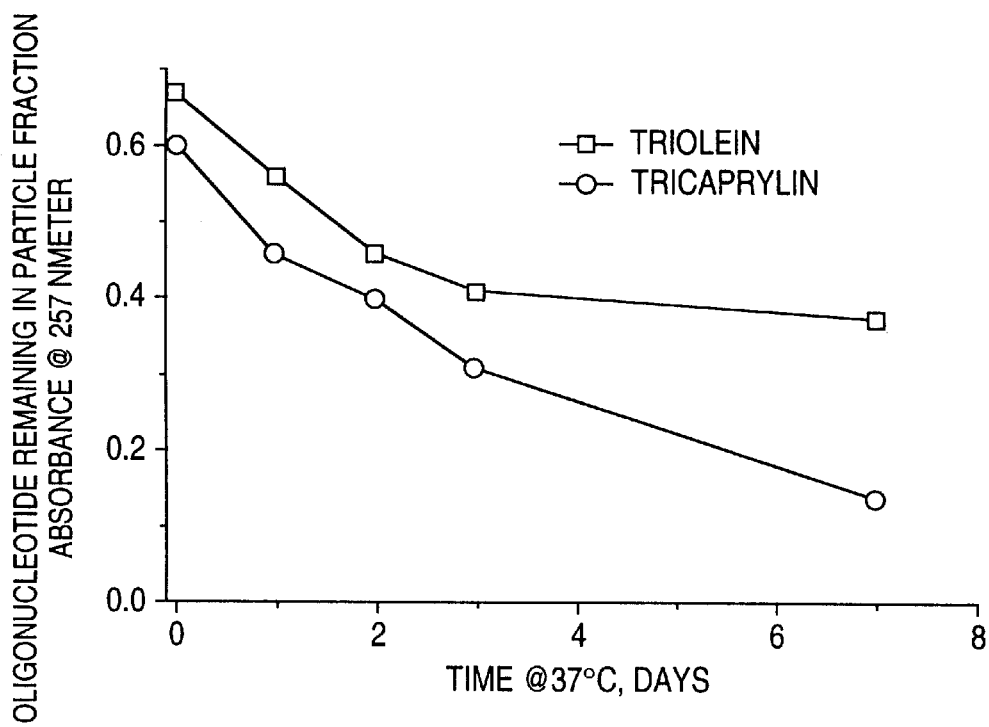

FIG. 15 is a graph showing the in vitro release of a 15-mer oligonucleotide from MVL prepared with triolein (□) or tricaprylin (○) as the neutral lipid. The MVL were incubated in rat cerebral spinal fluid (CSF) at 37° C.

Figure 16:
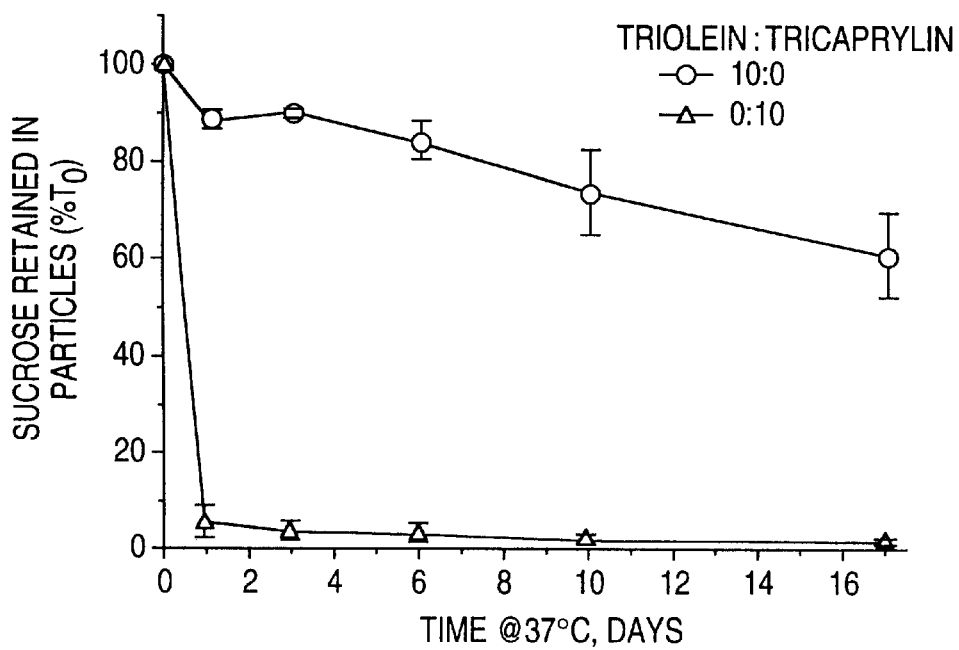

FIG. 16 is a graph showing the release during incubation in human plasma of 14C-sucrose from MVL also containing E. coli plasmid PBR 322 and lysine-hydrochloride. Sucrose release was used as a surrogate indicator of plasmid release. The MVL were manufactured with either (○) triolein or (Δ) tricaprylin as the neutral lipid.

Figure 17:
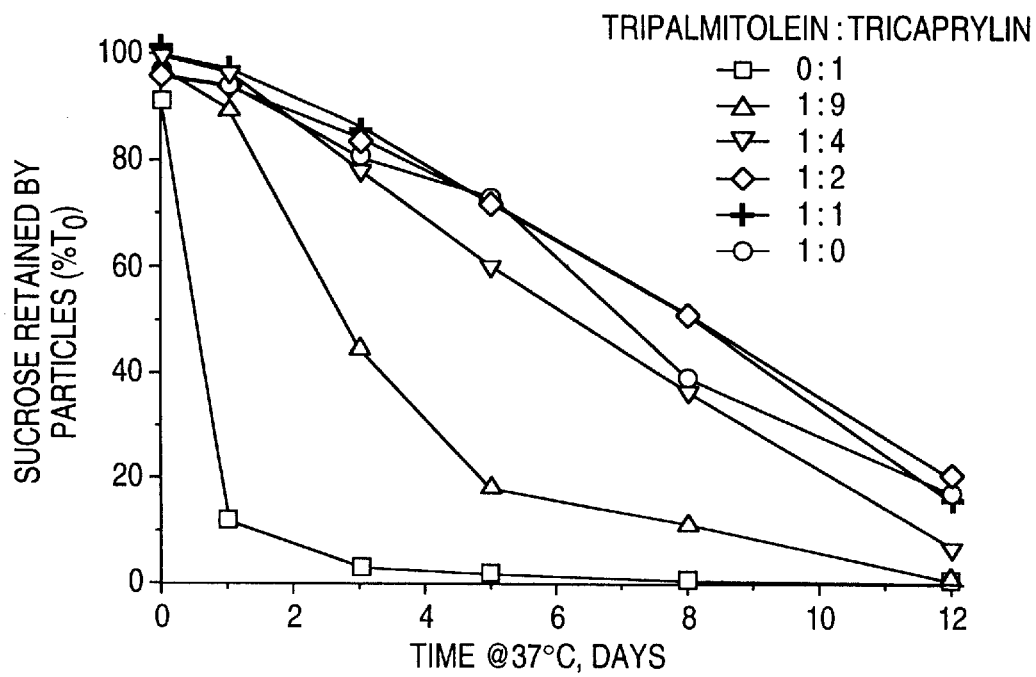

FIG. 17 is a graph showing the release of 14C-sucrose during incubation in human plasma of MVL manufactured with tripalmitolein and tricaprylin as the neutral lipid component. The neutral lipid ratio used in the MVL formulations were (○) tripalmitolein only; (+) 1:1 tripalmitolein:tricaprylin; (◇) 1:2 tripalmitolein:tricaprylin; (∇) 1:4 tripalmitolein:tricaprylin; (Δ) 1:9 tripalmitolein:tricaprylin; and (□) tricaprylin only.

Figure 18:
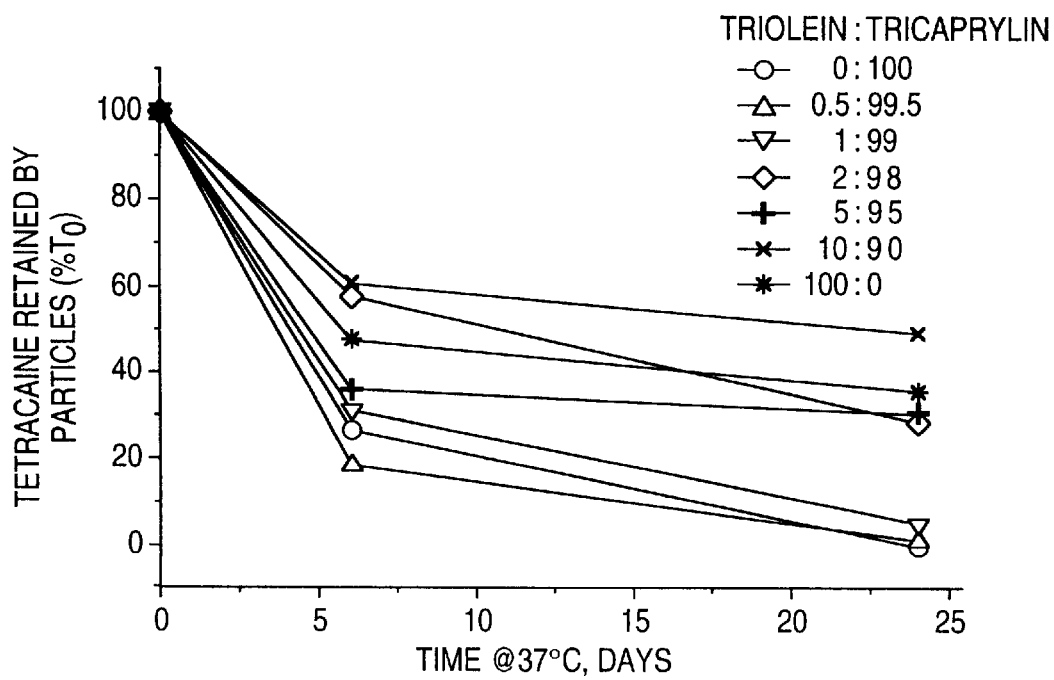

FIG. 18 is a graph showing the amount of tetracaine remaining at the subcutaneous injection site of mice injected with tetracaine containing MVL manufactured with a neutral lipid component of either (*) triolein; (X) 10:90, triolein:tricaprylin; (+) 5:95, triolein:tricaprylin; (◇) 2:98, triolein:tricaprylin; (∇) 1:99, triolein:tricaprylin; or (○) tricaprylin.

FIGS. 19A–D are graphs showing the release of MVL-encapsulated, biologically active compounds during storage in normal saline at temperatures of 2–8 (nominal 4), 25, 32, and 37° C. The MVL were manufactured with either tricaprylin (FIGS. 19A and 19C); or tricaprin (FIGS. 19B and 19D); as the neutral lipid component and with either cytosine arabinoside (FIGS. 19A and 19B); or morphine, FIGS. 19C and 19D) as the biologically active compound.

Figure 19A:
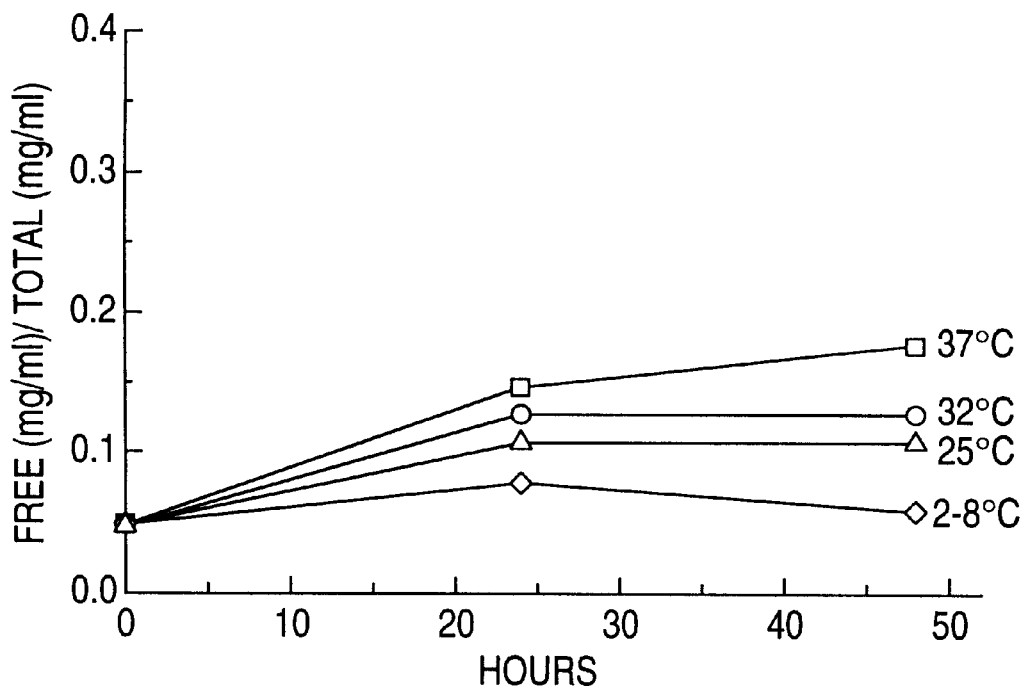
Figure 19B:
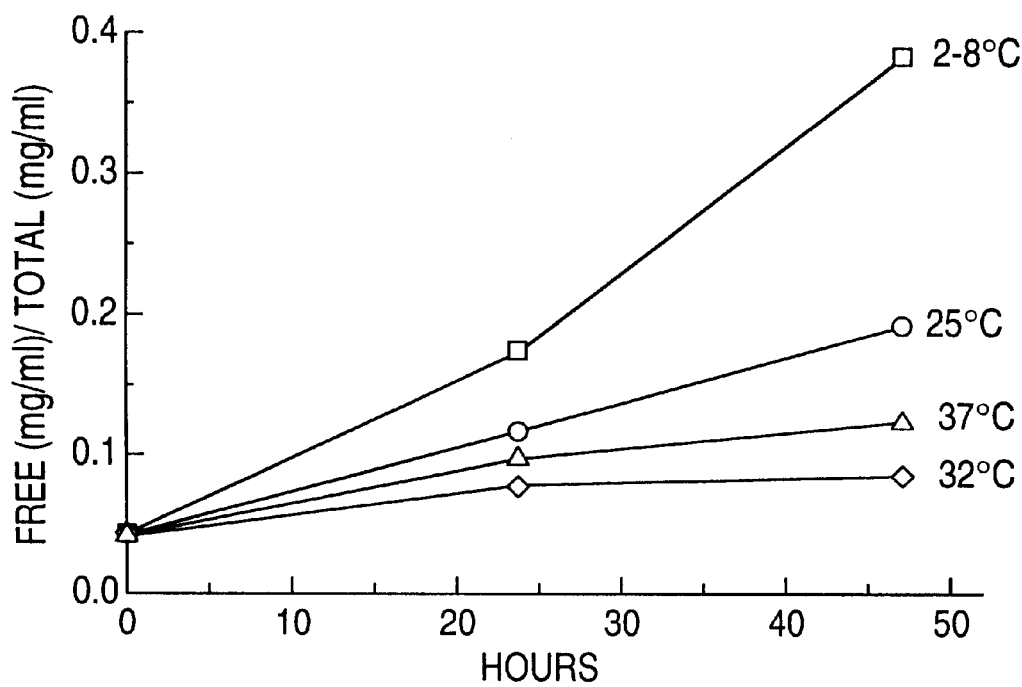
Figure 20:
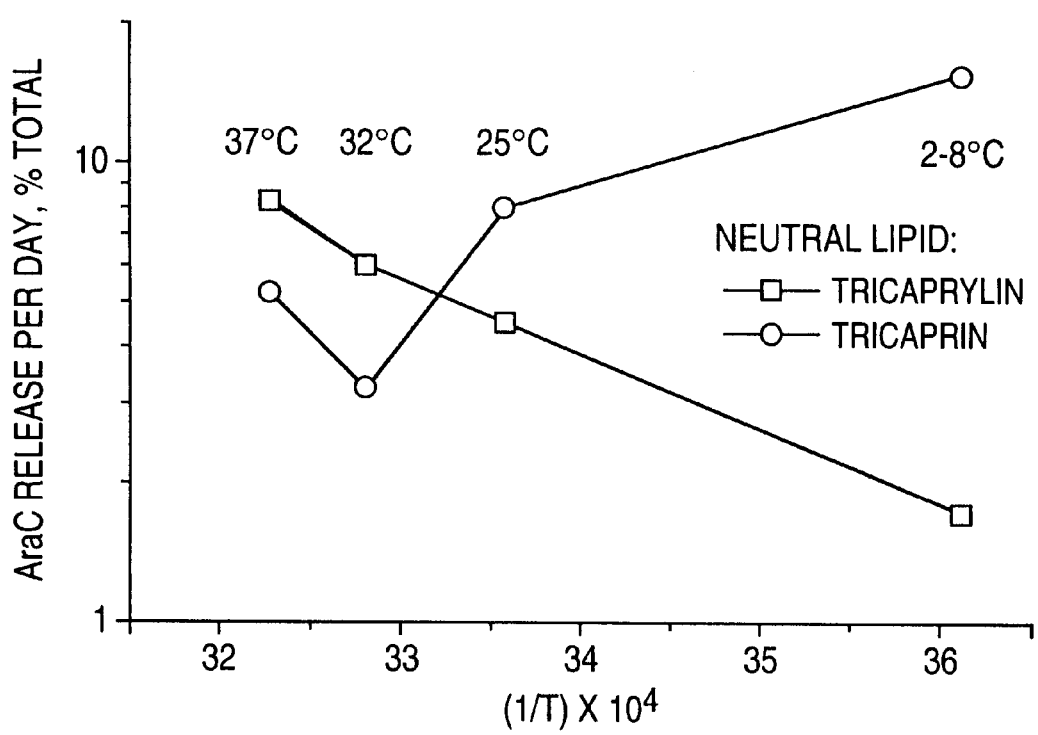

FIG. 20 is an Arrhenius plot of the graphs in FIGS. 19A and 19B showing the dependence of cytosine arabinoside release rate on the storage temperature of MVL manufactured with (□) tricaprylin, melting point (mp) 8° C.; or (○) tricaprin, mp 31.5° C., as the neutral lipid component. The abscissa is the inverse of storage temperature, °K.

DETAILED DESCRIPTION

A method is provided for modifying the rate of release of a biologically active compound, such as a drug, encapsulated in a multivesicular liposomal formulation by selection of the neutral lipid, or combination of neutral lipids, used to manufacture the multivesicular liposomes (MVL).

There are at least three types of liposomes. The term "multivesicular liposomes (MVL)" as used throughout the specification and claims means man-made, 1–200 μm particles partially comprised of lipid membranes enclosing multiple non-concentric aqueous chambers. In contrast, "multilamellar liposomes or vesicles" (MLV) have multiple "onion-skin" concentric membranes, in between which are shell-like concentric aqueous compartments. Multilamellar liposomes characteristically have mean diameters in the micrometer range, usually from 0.5 to 25 μm. The term "unilamellar liposomes or vesicles (ULV)" as used herein refers to liposomal structures having a single aqueous chamber, usually with a mean diameter range from about 20 to 500 nm.

Multilamellar and unilamellar liposomes can be made by several relatively simple methods. The prior art describes a number of techniques for producing ULV and MLV (for example U.S. Pat. No. 4,522,803 to Lenk; U.S. Pat. No. 4,310,506 to Baldeschweiler; U.S. Pat. No. 4,235,871 to Papahadjopoulos; U.S. Pat. No. 4,224,179 to Schneider, U.S. Pat. No. 4,078,052 to Papahadjopoulos; U.S. Pat. No. 4,394,372 to Taylor U.S. Pat. No. 4,308,166 to Marchetti; U.S. Pat. No. 4,485,054 to Mezei; and U.S. Pat. No. 4,508,703 to Redziniak).

By contrast, production of multivesicular liposomes requires several process steps. Briefly, the preferred method for making MVL is as follows: The first step is making a "water-in-oil" emulsion by capturing in a lipid component composed of at least one amphipathic lipid and at least one neutral lipid in one or more volatile organic solvents for the lipid component, an immiscible first aqueous component and a biologically active substance to be encapsulated, and optionally adding, to either or both the lipid component and the first aqueous component, an acid or other excipient for modulating the release rate of the encapsulated biologically active substances from the MVL. The mixture is emulsified, and then mixed with a second immiscible aqueous component to form a second emulsion. The turbulence required for formation of the second emulsion is provided either mechanically, by ultrasonic energy, nozzle atomization, and the like, or by combinations thereof, to form solvent spherules suspended in the second aqueous component. The solvent spherules contain multiple aqueous droplets with the substance to be encapsulated dissolved in them (see Kim et al., Biochem. Biophys. Acta, 728:339–348, 1983). For a comprehensive review of various methods of ULV and MLV preparation, refer to Szoka, et al. Ann. Rev. Biophys. Bioeng. 9:465–508, 1980.

The term "solvent spherule" as used throughout the specification and claims means a microscopic spheroid droplet of organic solvent, within which are multiple smaller droplets of aqueous solution. The solvent spherules are suspended and totally immersed in a second aqueous solution.

The term "neutral lipid" means an oil or fat that has no membrane-forming capability by itself and lacks a hydrophilic "head" group.

The term "amphipathic lipid" means a molecule that has a hydrophilic "head" group and hydrophobic "tail" group and has membrane-forming capability.

The term "zwitterionic lipid" means an amphipathic lipid with a net charge of zero at pH 7.4.

The term "anionic lipid" means an amphipathic lipid with a net negative charge at pH 7.4.

The term "cationic lipid" means an amphipathic lipid with a net positive charge at pH 7.4.

As used herein, the "shelf life" of a liposomal formulation is related to the rate of release of the encapsulated substance from a liposomal formulation in a storage solution, for instance normal saline (0.9% sodium chloride), at a storage temperature, for instance at 4° C.

In general, for making multivesicular liposomes, it is required that at least one amphipathic lipid and one neutral lipid be included in the lipid component. The amphipathic lipids can be zwitterionic, anionic, or cationic lipids. Examples of zwitterionic amphipathic lipids are phosphatidylcholines, phosphatidylethanolamines, sphingomyelins etc. Examples of anionic amphipathic lipids are phosphatidylglycerols, phosphatidylserines, phosphatidylinositols, phosphatidic acids, etc. Examples of cationic amphipathic lipids are diacyl trimethylammonium-propane and ethyl phosphatidylcholine. Examples of neutral lipids are triolein and tripalmitolein, trimyristolein and tricaprylin.

In the new method, the release rate of the biologically active compound is modified by utilizing in manufacture of the multivesicular liposomes a neutral lipid component that provides the desired rate of release in the type of fluid in which the MVL are to be used. For in vivo use, therefore, the release rate of the MVL must be determined in plasma or a plasma-like medium because the release rate of the biologically active compound from the MVL for certain neutral lipids can differ greatly depending on whether the release is into saline or plasma.

As used herein, the term "neutral lipid component" means the neutral lipid, or mixture of neutral lipids, used in manufacture of the multivesicular liposomes.

As used herein, the term "plasma-like medium," means a synthetic solution that includes in addition to normal saline, at least some of the protein or lipid constituents of blood plasma or components of other biological fluids, such as cerebro-spinal fluid (CSF), or interstitial fluids. For instance, normal saline containing citrated human plasma or bovine serum albumin (BSA) is an example of a "plasma-like medium" as the term is used herein.

The term "in vivo conditions" means actual injection or emplacement of MVL into a living body, and includes so-called "ex vivo" incubation of MVL in plasma or a plasma-like medium at body temperature (i.e., 37° C. for humans).

Although the neutral lipid component can comprise a single neutral lipid, generally the neutral lipid component comprises a mixture of a slow release neutral lipid and a fast release neutral lipid in a molar ratio range from about 1:1 to 1:100, e.g., from about 1:4 to 1:18, wherein the rate of release of the biologically active compound decreases in proportion with the increase in the ratio of the slow release neutral lipid to the fast release neutral lipid. For convenience, the molar ratio of the slow release neutral lipid to the fast release neutral lipid is referred to herein as "the slow:fast neutral lipid molar ratio."

The "slow release neutral lipid" used in the practice of this invention can be selected from triglycerides having monounsaturated fatty acid ester moieties containing from about 14 to 18 carbons in the acyl chain and generally having a molecular weight from about 725 to 885, and those with saturated fatty acid ester moieties containing from about 10 to 12 carbons in the acyl chain and generally having a molecular weight from about 554 to 639; and mixtures thereof, and cholesterol esters such as cholesterol oleate and esters of propylene glycol. The preferred slow release neutral lipids for use in the method of this invention are triolein, tripalmitolein, trimyristolein, trilaurin, and tricaprin, with triolein or tripalmitolein being most preferred. When in vivo use is contemplated, trilaurin (mp 46.5° C.) and other neutral lipids with a melting point above 37° C. are generally used in the practice of this invention only in mixture with one or more other neutral lipids wherein the mixture has a melting point temperature at or below, and preferably below 37° C. One skilled in the art will know how to determine the melting point of a mixture of lipids, such as a mixture of triglycerides.

The "fast release neutral lipid" used in the practice of this invention can be selected from triglycerides having monounsaturated fatty acid ester moieties containing from about 6 to 8 carbons in the acyl chain and having a molecular weight from about 387 to 471, and mixtures thereof. However, it has surprisingly been discovered that the use of a neutral lipid component in MVL containing one or more neutral lipids with an acyl chain of six or less carbons (especially use of tricaproin as the sole neutral lipid) results in rapid release of the encapsulated compounds upon contact with the in vivo environment. Therefore neutral lipids with an acyl chain of six or less carbons should be used only in combination with one or more neutral lipids having a longer chain acyl moiety. The preferred fast release neutral lipids are tricaprylin, and mixtures of tricaprylin and tricaproin, or mixed chain $C_6$ to $C_8$ triglycerides. Propylene glycol diesters with eight or ten carbon acyl moieties, cholesterol oleate, and cholesterol octanoate can also be used as neutral lipids.

A factor of equal importance to the molar ratio of neutral lipids is selection of a neutral lipid component having a melting point below the temperature at which the MVL is to be stored and/or used. As many biologically active compounds highly desirable in therapeutic applications require low storage temperature to prevent rapid deterioration, the neutral lipid component should be selected to have a melting point below the desired storage temperature as well as below the temperature at which the formulation will be used in vivo.

The results of storage temperature tests were determined by inspecting the particles microscopically and measuring by chemical assay the amounts of encapsulated material released. As is seen in these studies (FIG. 20), MVLs stored at a temperature below the melting point of the neutral lipid component undergo a structural reorganization of the membranes that is, in some cases, accompanied by rapid release ("dumping") of the encapsulated contents. This phenomenon is referred to herein as "the melting point effect." The time to onset of the melting point effect depends upon the neutral lipid composition and the ingredients of the encapsulated aqueous phase. Certain encapsulated compounds, such as IL-2, appear to interact with MVLs in such a way as to delay by hours or even days, the onset of "freezing" at temperatures below the melting point of the neutral lipid, perhaps by influencing formation in the MVL of an intermediate, "meta-stable" state. However, even formulations with such delayed onset eventually undergo the morphological transition characteristic of the melting point effect. Examples 15 and 16 below illustrate the melting point effect on the release rates of encapsulated biologically active compounds from MVL stored at a temperature below the melting point (FIGS. 19A–D and 20). To distinguish between the two states of morphological transition, the delayed onset effect is referred to herein as "the temperature effect."

In selecting the neutral lipid component in accordance with the practice of this invention, it is generally preferred that the neutral lipid component have a melting point at or above the temperature at which the MVL are to be stored and/or used (to prevent rapid loss of the encapsulated active compound either during storage or during in vivo use) due to the melting point effect. The melting point temperature of a neutral lipid component comprising a mixture of neutral lipids, and hence the temperature of the melting point effect on MVL containing the neutral lipid component, can readily be determined by preparing the mixture of interest and subjecting it to progressively lower temperatures until the mixture is observed to "freeze." One method of performing this procedure is disclosed in J. B. Rossell, *Advances in Lipid Research* 5: 353–408, 1967. One skilled in the art will be aware of other approaches that can be used to obtain this information. However, it should be remembered that the melting point effect upon the liposomal formulation as a whole can be influenced by the other lipids in the MVL as well as by the ingredients in the first aqueous solution.

Table 1 below lists the number of carbons in the acyl chains, the molecular weight, and melting point temperatures of representative neutral lipids that can be used in the practice of this invention.

TABLE 1

The Physical Properties of Neutral Lipids

| Neutral lipid | Fatty Acid Ester | Mol. Wt. | Viscosity cP | M.P. ° C. |
|---|---|---|---|---|
| TriGlycerides | | | | |
| Triolein | C18:1 9C | 885 | 74 | 5 |
| Tripalmitolein | C16:1 9C | 801 | | ≦5 |
| Trimyristolein | C14:1 9C | 725 | ≦5 | |
| Trilaurin | C12 | 639 | | 45.5 |
| Tricaprin | C10 | 555 | | 31.5 |
| Tricaprylin | C8 | 471 | 20–28 | 8.3 |
| Tricaproin | C6 | 387 | | ≦0 |
| Captex 355 Propylene Glycol Diester | C8, C10 mixed | Avg. 496 | | ≦5 |
| Captex 200 Cholesterol Ester | C8, C10 mixed | Avg. 345 | 9–13 | ≦5 |
| Cholesterol Oleate | C18:1 9C | 651 | | 44–47 |
| Cholesterol Octanoate | C8 | 512 | | 110 |

In one method of the invention, the release rate of the biologically active compound is modified by utilizing in manufacture of the multivesicular liposomes a neutral lipid component comprising triolein or tripalmitolein, or a mixture thereof, as the slow release neutral lipid, and selecting a molar ratio of the slow release neutral lipid to a fast release neutral lipid in the range from about 1:0 to 0:1. The rate of release of the active compound increases with the increase in the proportion of the fast release neutral lipid in the molar ratio. Generally the molar ratio of the neutral lipid component to the sum of all the lipids in the MVL formulation is in the range from about 0.01 to about 0.21. The preferred fast release neutral lipid for use in such formulations with triolein and/or tripalmitolein is tricaprylin.

In addition to the melting point effect, which is contributed in part by the neutral lipid component, the characteristics of the aqueous phase encapsulated in the MVL, particularly the chemical interaction of the active compound with the lipids in the MVL, can also influence the rate of release of the biologically active compound. To take this additional factor into account during formulation, in one embodiment this invention provides a method of tailoring the neutral lipid component to the aqueous phase of interest.

In the first step of the method, to determine how the neutral lipid component functions with any specific aqueous phase (i.e., one containing a biologically active compound of interest), a family of MVL formulations is made containing the aqueous phase of interest, wherein each member of the family of formulations contains a different slow:fast release neutral lipid molar ratio of the selected slow and fast release neutral lipids such that the family as a whole represents a graded progression of such ratios, for example 1:1, 1:2, 1:4, 1:9, 1:18; 1:27, 1:100, etc.

The in vivo release rates corresponding to the various slow:fast neutral lipid molar ratios embodied in the individual members of the family of MVL formulations is determined by separately incubating each member of the family in vitro in plasma or a plasma-like medium at in vivo temperature, i.e. 37° C. for humans, for a period of hours, or even days.

Any of the methods illustrated in the Examples, or others known to one of skill in the arts, can be used to determine at progressive time points the cumulative amount of one or more substance(s) encapsulated with the aqueous phase that has been released during incubation. For ease in making this determination, a radioactive substance, such as $^{14}C$ sucrose, can be included in the aqueous phase at the time of encapsulation. However, it is preferred to select the biologically active compound of interest as the substance whose release rate is monitored and recorded. It is recommended that the release rate information be obtained in this manner for each member of the family of formulations being tested.

From the release rate information determined by this procedure, a graph showing a release curve, or "release rate profile" can be plotted for each member of the family of formulations to show its individual in vivo release characteristics, with the ordinate of the graph indicating the cumulative amount of the substance of interest that has either been released or retained, and the abscissa indicating progressive time points at which the amount released or retained is measured. A corresponding family of rate release curves is thus generated, with each curve of the family illustrating the release characteristics of its corresponding slow:fast neutral lipid molar ratio when used with the aqueous phase being tested.

The skilled practitioner can then select the formulation having the most desirable release characteristics for the particular therapeutic application of interest to obtain the desired control over release of the substance of interest (i.e., a biologically active compound) so as to deliver a therapeutically effective amount of the active compound to the individual to be administered the MVL formulation. A skilled practitioner can thus select a MVL formulation, in particular one having the most advantageous slow:fast neutral lipid molar ratio, for delivering a therapeutically effective dose over the optimum period of time so as to maximize the therapeutic effect of the drug or other biologically active compound administered during therapy.

For instance, if it is desired to produce a MVL formulation that releases a particular active compound in vivo in a relatively short period of time, i.e., over several hours after administration, the neutral lipid component that yields a release curve indicating such delivery characteristics when stored in vitro in plasma, or a plasma-like composition, at about 37° C. will be selected. The proportion of the fast release neutral lipid in the ratio will be comparatively large in this circumstance. On the other hand, when it is desired to produce a MVL formulation that releases its active compound in vivo over a relatively long period of time, i.e., over tens of hours after administration, even up to 200 hours post administration, the neutral lipid component that yields a release curve indicating such delivery characteristics when incubated under in vivo conditions will be selected. In this case the proportion of the slow release neutral lipid in the molar ratio will be comparatively large, and in some instances the neutral lipid component will contain no fast release neutral lipid at all.

The shelf-life stability of the formulations should also be determined by incubation of the formulations in the contemplated storage medium at whatever storage temperature is required to assure integrity of the biologically active compound for a suitable period of time. For convenience, the self-life stability tests can also be conducted in plasma or a plasma-like medium, but one skilled in the art will be able to substitute a different suitable storage medium, such as normal saline, for use with the biologically active compound of interest, if desired. Since many biologically active compounds require storage at temperatures in the range from about 2 to 8° C., it is recommended that the shelf-life stability tests be conducted at a temperature in this range.

These procedures are illustrated in the Examples of this application. For instance, in formulations containing mixtures of triolein and tricaprylin, when the neutral lipid component was held constant and incremental increases in the ratio of triolein to tricaprylin were made, MVL formulations characterized by increasingly slower release were obtained, as is illustrated in Example 14 (FIG. 18). In Example 13, a graded family of formulations encapsulating sucrose and lysine-HCl and containing mixtures of tripalmitolein and tricaprylin were prepared. A graded family of formulations was created with tripalmitolein:tricaprylin molar ratios of 0:1, 1:0, 1:9, 1:4, 1:2, and 1:1 by holding constant the amount of tripalmitolein and making incremental increases in the amount of tricaprylin. In this Example, increasingly more rapid release was obtained for each incremental increase in the proportion of tricaprylin in the neutral lipid component.

Figure 14:
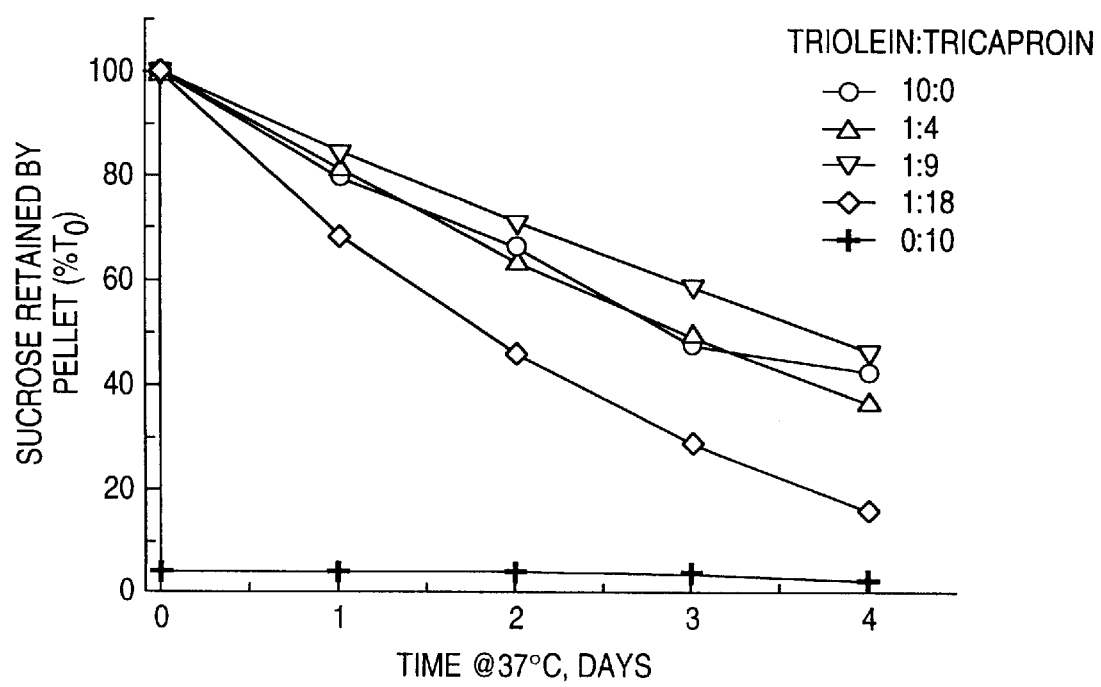
FIG. 14 is a graph showing the effect of using tricaproin as the neutral lipid component alone or in combination with triolein on the release of 14C-sucrose from MVL incubated in human plasma at 37° C. The formulations were ($\bigcirc$)

It should particularly be noted that, unlike most other types of liposomes, accurate in vivo release characteristics regarding MVL formulations cannot be predicted from in vitro release studies conducted in saline. For instance, MVL formulated with tricaproin, a triglyceride having only 6 carbons in its acyl moieties, as the only neutral lipid were not stable under in vivo conditions (in solutions containing plasma or serum albumin at 37° C., but were stable under storage conditions (in saline at 2–8° C. for up to a week). However, formulations containing tricaproin:triolein molar ratios of 4:1, 9:1, and 18:1 were stable under in vivo conditions for at least 4 days, and yielded a graded set of release rate curves (FIG. 14).

In another embodiment, the present invention provides liposomal compositions comprising a therapeutically effective amount of a biologically active compound encapsulated in a multivesicular liposome formulation wherein the formulation comprises a neutral lipid component with a molar ratio of slow release neutral lipid to fast release neutral lipid in the molar ratio range from about 0:1 to 1:0, for example 1:1 to 1:100 and generally from about 4:1 to 27:1. The molar ratio of the neutral lipid component to the sum of the lipids in the MVL formulation is generally in the range from about 0.01 to about 0.21.

The preferred amphipathic lipids for use in making the multivesicular liposomes are phospholipids with even numbers of carbons in the carbon chain because such phospholipids are natural lipids found in the body and do not produce toxic metabolites. A representative list of amphipathic lipids preferred for use in the practice of this invention follows. Also included are abbreviations that may be used to refer to particular phospholipids in this application. DOPC or DC18:1PC=1,2-dioleoyl-sn-glycero-3-phosphocholine DLPC or DC12:0PC=1,2-dilauroyl-sn-glycero-3-phosphocholine DMPC or DC14:0PC=1,2-dimyristoyl-sn-glycero-3-phosphocholine DPPC or DC16:0PC=1,2-dipalmitoyl-sn-glycero-3-phosphocholine DSPC or DC18:0PC=1,2-distearoyl-sn-glycero-3-phosphocholine DAPC or DC20:0PC=1,2-diarachidoyl-sn-glycero-3-phosphocholine DBPC or DC22:0PC=1,2-dibehenoyl-sn-glycero-3-phosphocholine DC16:1PC=1,2-dipalmitoleoyl-sn-glycero-3-phosphocholine DC20:1PC=1,2-dieicosenoyl-sn-glycero-3-phosphocholine DEPC or DC22:1PC=1,2-dierucoyl-sn-glycero-3-phosphocholine DPPG=1,2-dipalmitoyl-sn-glycero-3-phosphoglycerol DOPG=1,2-dioleoyl-sn-glycero-3-phosphoglycerol The term "biologically active compound" as used herein means a chemical compound that is known in the art as having utility for modulating biological processes so as to achieve a desired effect in modulation or treatment of an undesired existing condition in a living being, such as a medical, agricultural or cosmetic effect. Thus, biologically active compounds are generally selected from the broad categories of medicaments, pharmaceuticals, radioisotopes, agricultural products, and cosmetics.

Therapeutic biologically active compounds, or drugs for encapsulation in the methods and compositions of this invention include anti-neoplastic agents, anti-infective agents, hormones, anti-depressives, antiviral agents, anti-nociceptive agents, anxiolytics and biologics.

Representative examples of anti-neoplastic agents useful in the compositions and methods of the present invention include methotrexate, taxol, tumor necrosis factor, chlorambucil, interleukins, etoposide, cytarabine, fluorouracil and vinblastine.

Representative examples of anti-infective agents useful in the compositions and methods of the present invention include pentamidine, metronidazole, penicillin, cephalexin, tetracyclin and chloramphenicol.

Representative examples of anti-viral agents useful in the composition and methods of the present invention include dideoxycytidine, zidovudine, acyclovir, interferons, dideoxyinosine and ganciclovir.

Representative examples of anxiolytics and sedatives useful in the compositions and methods of the invention include benzodiazepines such as diazepam, barbiturates such as phenobarbital and other compounds such as buspirone and haloperidol.

Representative examples of hormones useful in the compositions and methods of the present invention include estradiol, prednisone, insulin, growth hormone, erythropoietin, and prostaglandins.

Representative examples of anti-depressives useful in the compositions and methods of the present invention include fluoxetine, trazodone, imipramine, and doxepin.

Representative examples of anti-nociceptives useful in the compositions and methods of the present invention include hydromorphine, oxycodone, fentanyl, morphine and meperidine.

The term "biologics" encompasses nucleic acids (DNA and RNA), proteins and peptides, and includes compounds such as cytokines, hormones (pituitary and hypophyseal hormones), growth factors, vaccines etc. Of particular interest are interleukin-2, insulin-like growth factor-1, interferons, insulin, heparin, leuprolide, granulocyte colony stimulating factor (GCSF), granulocyte-macrophage colony stimulating factor (GM-CSF), tumor necrosis factor, inhibin, tumor growth factor alpha and beta, Mullerian inhibitory substance, calcitonin, and hepatitis B vaccine.

The biologically active compound can be employed in the present invention in various forms, such as molecular complexes or biologically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium), and the like. Furthermore, derivatives of the active substances such as esters, amides, and ethers which have desirable retention and release characteristics, but which are readily hydrolyzed in vivo by physiological pH or enzymes, can also be employed.

As used herein the term "therapeutically effective amount" means the amount of a biologically active compound necessary to induce a desired pharmacological effect. The amount can vary greatly according to the effectiveness of a particular active substance, the age, weight, and response of the individual host as well as the nature and severity of the host's symptoms. Accordingly, there is no upper or lower critical limitation upon the amount of the active substance. The therapeutically effective amount to be employed in the present invention can readily be determined by those skilled in the art.

It is believed that the neutral lipid component in MVL, which is unique to MVL among liposomal formulations, interacts with the in vivo environment in such a way as to affect the rate at which compounds encapsulated within the MVL are released. In particular, MVL having a neutral lipid component comprised of triglycerides with less than 6 carbons in the acyl moiety interact with the in vivo environment so as to become completely destabilized virtually upon contact with blood plasma. For this reason, saline solutions do not accurately mimic the effect of the in vivo environment on the drug release characteristics of MVL, but it has been discovered that in vitro release studies conducted using blood plasma or a plasma-like medium can be used to accurately determine the in vivo release characteristics of an MVL formulation.

The following examples illustrate the manner in which the invention can be practiced. It is understood, however, that the examples are for the purpose of illustration, and the invention is not to be regarded as limited to any of the specific materials or conditions therein.

EXAMPLE 1

G-CSF-Containing MVL

1. Manufacture

For manufacture of multivesicular liposomes (MVL) containing granulocyte colony stimulating factor (G-CSF), the lipid combination solution contained (per ml chloroform): 11 mg DOPC, 2.3 mg DPPG, 8.7 mg cholesterol and either 2.4 mg (2.7 umol) triolein or 1.3 mg (2.7 umol) tricaprylin. Lipid solutions which contained four different molar ratios of the neutral lipids triolein and tricaprylin were prepared by mixing appropriate volumes of the triolein and tricaprylin containing lipid solutions. The molar ratios of triolein to tricaprylin were 100:0, 50:50, 25:75, 10:90, and 0:100.

The first aqueous phase solution for MVL formulations contained 174 mM glycine, 100 mM HCl, 0.001% Tween80™, and 100 μg/ml G-CSF, 1 ml was added to a vial containing 1 ml of the lipid combination and emulsified by fixing the capped vial in a horizontal configuration to the head of a vortex mixer (Scientific Products) and shaking at maximum speed (2400 oscillations/min.) for 6 minutes.

The final emulsion (2 ml) was divided and transferred to two vials containing 2.5 ml 3.2% glucose and 40 mM lysine. The emulsion was dispersed into microscopic droplets by fixing the capped vial in a horizontal configuration to the head of a vortex mixer and shaking for 3 seconds at 2400 oscillations/min. The contents of the vial were transferred to a flask containing 5 ml of 3.2% glucose, 40 mM lysine. The chloroform was removed from the microscopic droplets or spherules by transferring the flask to a 37° C. gyrorotary water bath and flushing the surface of the suspension with nitrogen gas at a flow rate of 10–15 cfh for 10 minutes. Multivesicular liposomes in suspension containing encapsulated G-CSF were obtained.

The particle suspensions were diluted 1:4 with normal saline, and the particles were harvested by centrifugation at 800×g for 10 minutes. The supernatant solution was removed by aspiration, and the particles were washed twice by resuspension in fresh, normal saline solution and centrifugation. The final washed product was resuspended at 25% packed-particle volume per total volume and stored at 2–8° C. for subsequent studies.

2. In Vitro Release Rate

The in vitro release rate of the MVL prepared as described above was determined by incubation in saline solutions containing 70% citrated-human plasma and 0.1% sodium azide at 37° C. G-CSF was determined in the centrifuge-collected particle fraction by solubilization of samples in 50% IPA and quantitation by high pressure liquid chromatography and UV detection using known methods.

Figure 1:
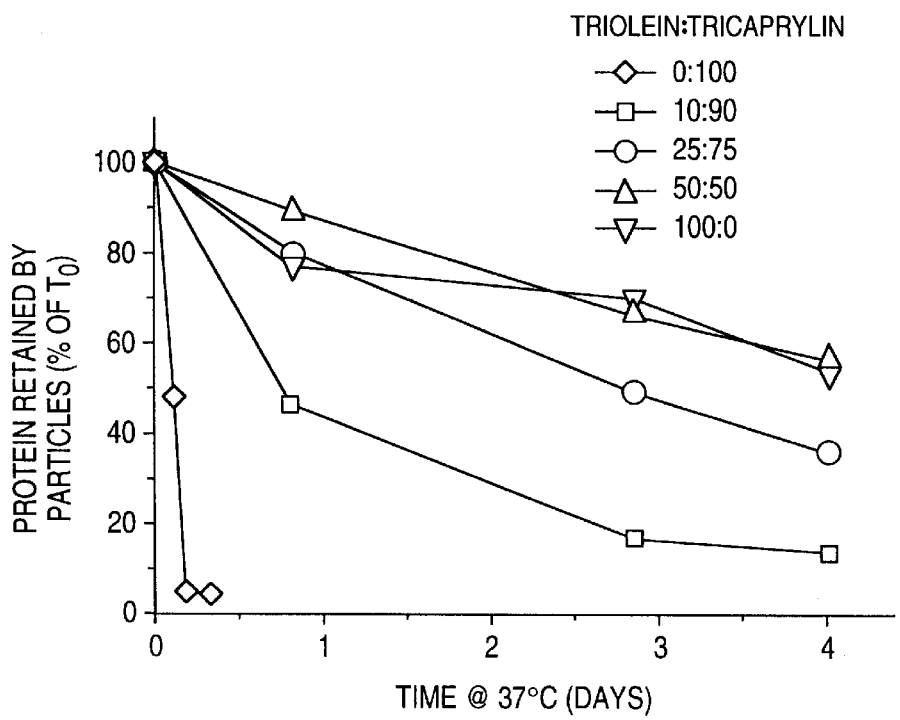
FIG. 1 is a graph comparing the release rates of recombinant, human granulocyte colony stimulating factor (rhu G-CSF) from multivesicular liposomes (MVL) formulated with different molar ratios of triolein to tricaprylin ($\nabla$, 100:0; $\Delta\Delta$, 50:50; $\bigcirc$, 25:75; $\square$, 10:90; $\diamond$, 0:100) as the neutral lipid when incubated at 37° C. in 60% human plasma in saline solution.

The dependence of the in vitro release rate of G-CSF on the composition of the neutral lipid component used in manufacture of the multivesicular liposomes is shown in FIG. 1. As the triolein to tricaprylin molar ratio was increased, the rate of release of G-CSF from the multivesicular liposomes decreased.

3. In Vivo Release Rate

The triolein and tricaprylin MVL formulations of G-CSF were evaluated in a pharmacodynamic model in Syrian Golden Hamsters. Exogenous G-CSF stimulates neutrophil (granulocyte) production which can be evaluated by assaying blood samples for an increase in peripheral blood neutrophil number and correspondingly an increase in peripheral blood leukocyte number.

Therefore, the formulations containing tricaprylin or triolein were evaluated for release in a pharmacodynamic hamster model that measured peak and duration of excess leukocyte (granulocyte) production caused by rhu G-CSF (Cohen et al. 1987, *Proc. Natl. Acad. Sci. USA*, 84:2484–2488). In these studies the subcutaneous injection of a solution of G-CSF was used as a control for bioequivalence of the encapsulated protein. The rapid-release formulation containing tricaprylin was also used as a control for bioequivalence of the encapsulated protein. First, the peak and duration of granulocyte increase upon subcutaneous injection of hamsters with formulations containing all tricaprylin (slow:fast molar ratio of 0:100) was compared against that caused by a solution of unencapsulated G-CSF and the longer-release duration triolein formulation (slow:fast mole ratio of 100:0). For each formulation, 3 to 5 hamsters received 75–100 ug G-CSF per kg. The results (FIG. 2), are as predicted by the in vitro release studies. The tricaprylin formulation provided a rapid release of G-CSF and stimulated granulocyte production similar to that of the unencapsulated G-CSF solution. The triolein formulation had a lower (and later) peak and longer duration.

Figure 2:
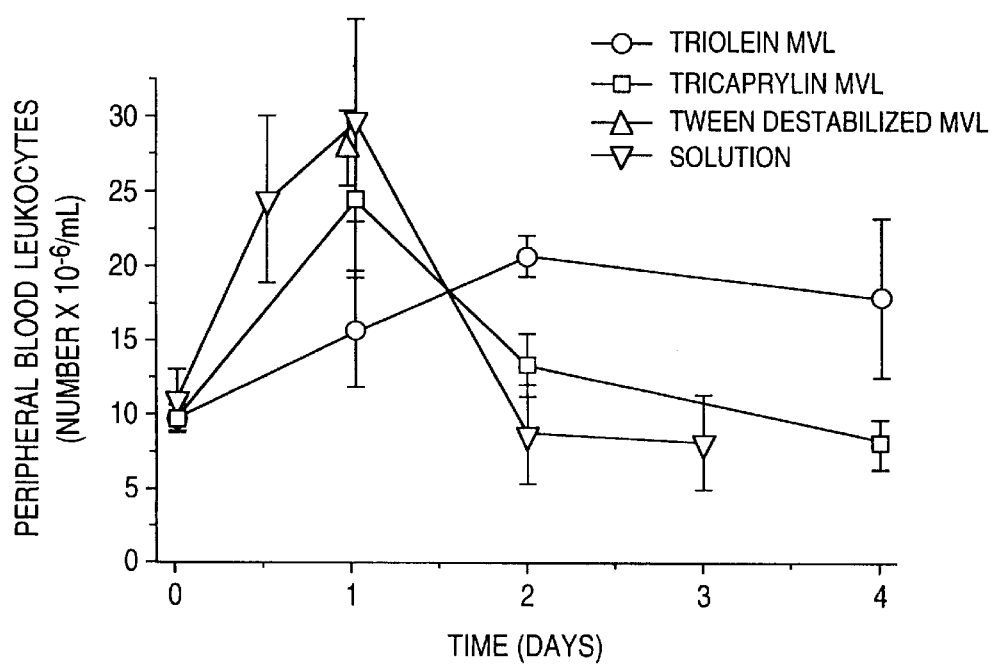
FIG. 2 is a graph showing the results of a pharmacodynamic study comparing the duration of the rhu G-CSF dependent elevation in peripheral blood leucocyte number of golden Syrian hamsters following subcutaneous injection of 100 $\mu$g/kg of rhuG-CSF in saline solution ($\nabla$), in a triolein-only, 100:0, MVL formulation ($\bigcirc$), in a triolein-only MVL formulation solubilized pre-injection with Tween™ 20 ($\Delta$), and in a tricaprylin-only, 0:100, MVL formulation ($\square$)

As a further control, a group of hamsters were injected with the triolein formulation solubilized with detergent (Tween 20™) immediately prior to injection. The granulocyte number found at 24 hours for the solubilized formulation was similar to that observed resulting from injections of the G-CSF-solutions or the formulation containing only tricaprylin as the neutral lipid (FIG. 2).

EXAMPLE 2

1. Manufacture

Multivesicular liposomes containing granulocyte/macrophage-colony stimulating factor (GM-CSF) were manufactured as described in Example 1, but using neutral lipid molar ratios of triolein to tricaprylin of 100:0, 25:75 and 10:90.

2. In Vitro Release in Human Plasma at 37° C.

The suspensions were prepared and incubated in human plasma at 37° C. as described in Example 1. GM-CSF remaining encapsulated was determined by solubilization of the particle fraction in 50% IPA and quantitation by high pressure liquid chromatography and UV detection using known methods.

Figure 3:
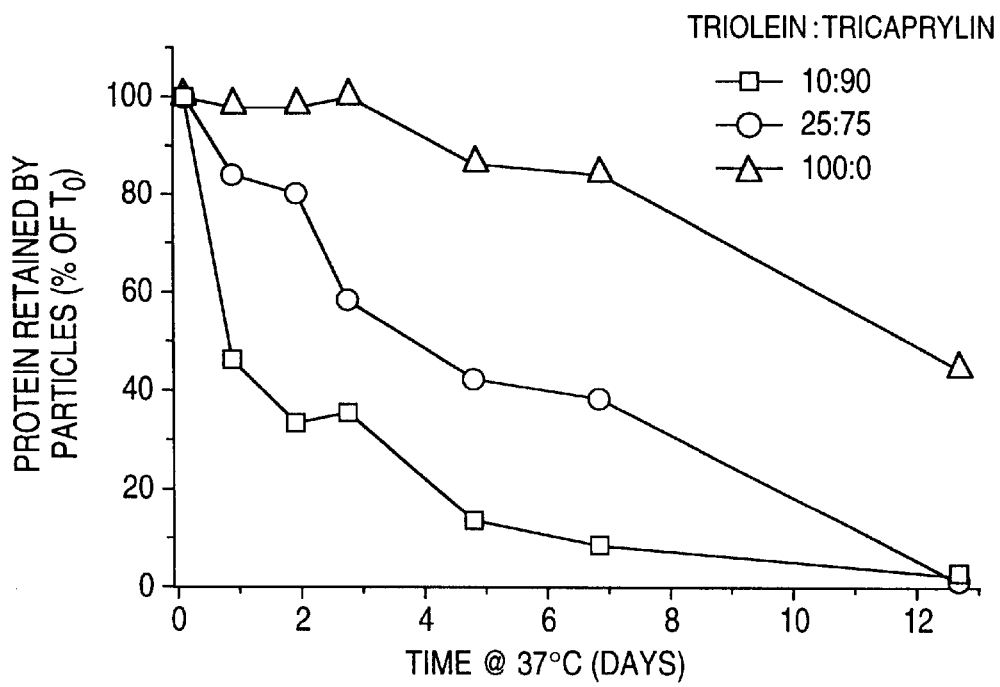
FIG. 3 is a graph comparing the release rates of rhu GM-CSF from MVL formulated with different molar ratios of triolein to tricaprylin ($\Delta$, 100:0; $\bigcirc$, 25:75; $\square$, 10:90) as the neutral lipid when incubated at 37° C. in 60% human plasma in saline solution.

The results of the in vitro release assay (FIG. 3) demonstrate that the graded replacement of triolein with tricaprylin results in graded increases in release rate.

3. In Vitro Pharmacokinetics

Figure 4:
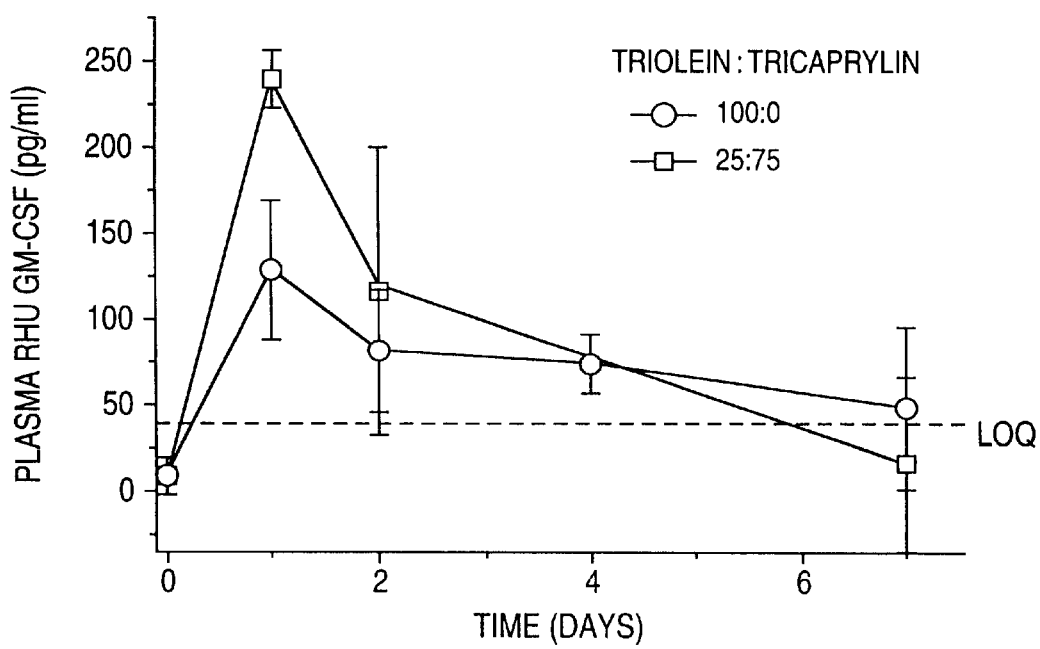
FIG. 4 is a graph showing a pharmacokinetic study of levels of rhu GM-CSF in venous blood, plasma samples of mice following a subcutaneous injection of 1 mg/kg rhu GM-CSF in the triolein-only, 100:0, MVL formulation ($\bigcirc$) and in the 25:75, triolein:tricaprylin MVL formulation ($\square$). The rhu GM-CSF level in EDTA-plasma was determined by ELISA. LOQ is the limit of quantitation.

BALBc mice (aged 7 to 8 weeks and weighing approximately 20 grams) were administered subcutaneous injections of liposomes containing GM-CSF manufactured with either 100% triolein or a 25:75 ratio of triolein to tricaprylin. Blood samples were collected before the injection and at 1, 2, 4, and 7 days post injection, and the plasma was assayed for GM-CSF concentration using an ELISA kit. The formulation manufactured with 25:75 triolein to tricaprylin provided a higher peak level and a shorter duration of detectable rhu GM-CSF compared to the formulation manufactured with 100% triolein as the neutral lipid (FIG. 4). These results are as predicted by the in vitro assay in human plasma at 37° C., and show that the rate of release of encapsulated GM-CSF is increased by addition of tricaprylin to the neutral lipid component.

EXAMPLE 3

Depo/IGF-1

1. Manufacture

Multivesicular liposomes were manufactured with rhu IGF (recombinant human insulin-like growth factor), with $^{14}C$-sucrose as an osmotic spacer, and ammonium citrate as a buffer. The lipid combination solution contained (per liter) 10.4 g DOPC, 2.1 g DPPG, 7.7 g cholesterol, and the triglyceride component was either 2.1 g triolein, 1.9 g tripalmitolein, 1.5 g trilaurin, 1.3 g tricaprin, or 1.1 g tricaprylin (molar ratio, 0.34:0.07:0.52:0.06).

The first aqueous phase solution contained (per ml) 16 mg rhu IGF-1 (Chiron), 7% sucrose, and 20 mM ammonium citrate, pH 5. A first emulsion was made by high-speed mixing of 5 ml of the lipid combination solution with 5 ml of the aqueous phase solution at 9000 rpm for 9 minutes at 25–27° C. The emulsion was sheared into microdroplets (spherules) by addition of 30 ml 40 mM lysine, 4% glucose solution to the mixing vessel and mixing at 6000 rpm for 1 min. The chloroform was removed from the microscopic droplets or spherules by transferring the suspension to a flask containing 70 ml of 40 mM lysine, 3.2% glucose solution, placing the flask in 37° C. gyrorotary water bath, and flushing the surface of the suspension with nitrogen gas at a flow rate of 70 cfh for 20 minutes to obtain the MVL particles in suspension.

The suspensions were diluted 1:4 with normal saline, and the particles were harvested by centrifugation at 800×g for 10 minutes at room temperature. The supernatant solution was removed by aspiration, and the particles were washed twice by resuspension in fresh, normal saline solution and centrifugation.

2. In Vitro Release Rates

Figure 5:
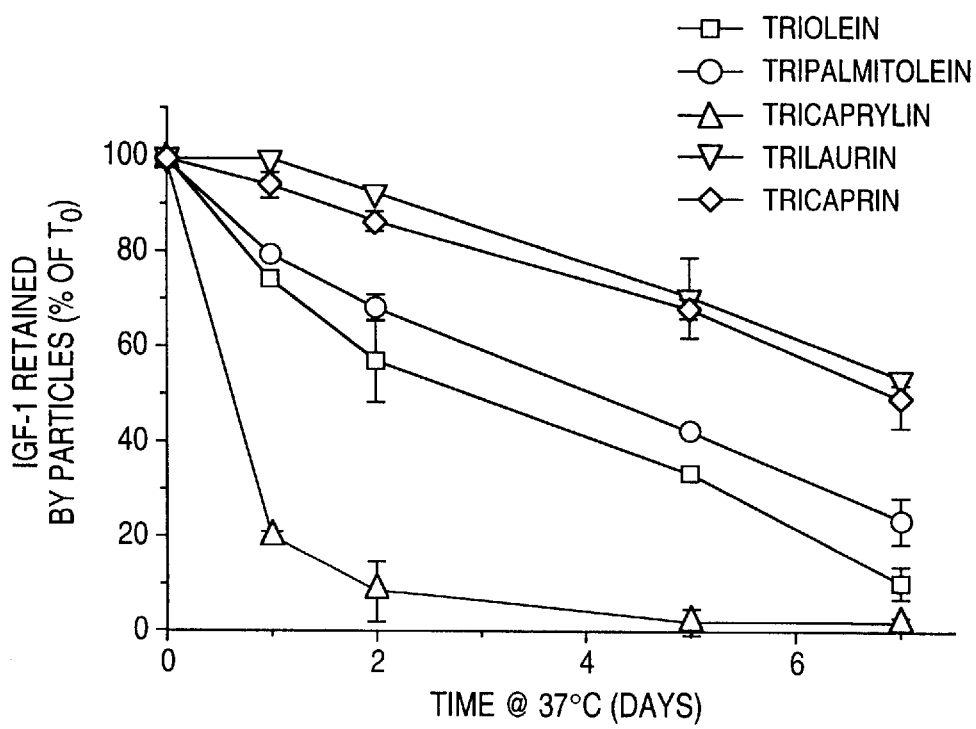
FIG. 5 is a graph showing the release rates of rhu IGF-1 from multivesicular liposomes formulated with various triglycerides as the neutral lipid component when incubated at 37° C. in 60% human plasma in saline solution. The neutral lipids used in MVL manufacture were: ($\square$) triolein, ($\bigcirc$) tripalmitolein, ($\Delta$) tricaprylin, ($\nabla$) trilaurin, and ($\diamond$) tricaprin.

The final washed product was resuspended at 25% packed-particle volume per total volume and stored at a temperature of 2–8, 25, 32, or 37° C. for either 24 or 48 hours. The pellet fraction from the 25,000×G×2 minute centrifugation was solubilized and assayed by HPLC for IGF-1 retained. Also, each of the IGF-1-containing formulations stored at 2–8° C. was evaluated within 24 hours in the in vitro release assay described in Example 1 and the results are summarized in FIG. 5. The formulations manufactured with triolein (C18:1) or tripalmitolein (C16:1) showed a similar release rate profile. Greater than 70% of the encapsulated IGF-1 released in 7 days. The formulation manufactured with tricaprylin (C8) demonstrated a rapid release rate profile with nearly complete release of IGF-1 in 2 days. The formulations manufactured with tricaprin (C10) or trilaurin (C12) released IGF-1 markedly more slowly than the standard triolein formulation, less than 50% released in 7 days. These results suggest that the acyl chain length of the triglyceride is not directly correlated with the rate of release of encapsulated IGF-1 in vitro, because the release of the tricaprylin (C8) formulations was more rapid than that of the tricaprin (C10) or trilaurin (C12) formulations.

It should be noted that storage of the trilaurin formulations in saline for only a few days at 2–8° C. resulted in morphological reorganization of the particles and an accompanying complete release of encapsulated materials. This effect would not be expected from the stability exhibited in the in vitro release assay at higher temperatures. This catastrophic effect was related to storage of the formulation at temperatures significantly lower than the freezing point of the neutral lipid. This effect is demonstrated in Examples 16 and 17 below.

3. In Vivo Pharmacokinetics

Figure 6:
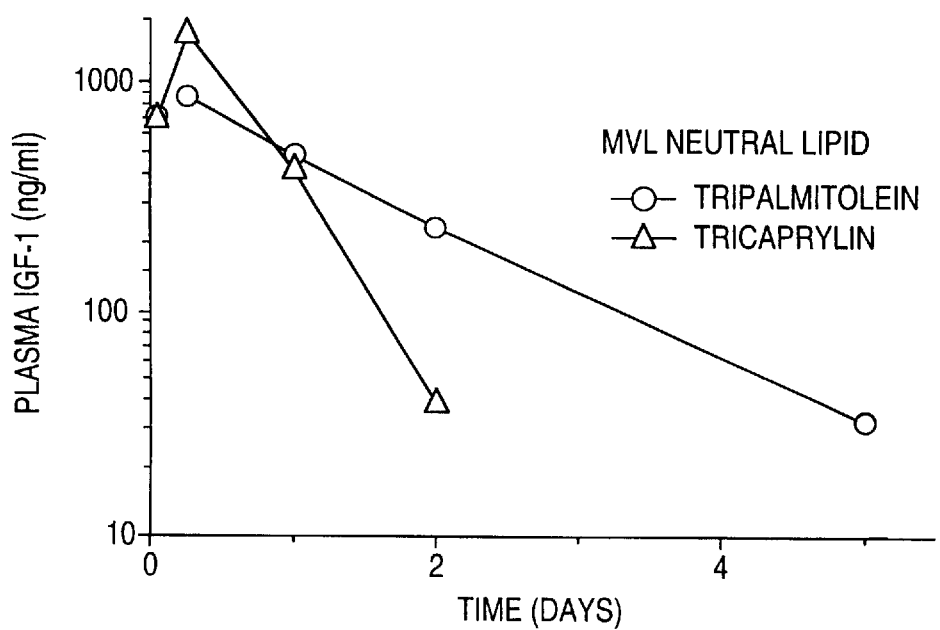
FIG. 6 is a graph showing the results of a pharmacokinetic study of levels of rhu IGF-1 in serum of rats following subcutaneous injection of 6.25 mg/kg rhu IGF-1 in the tripalmitolein MVL formulation ($\bigcirc$) and in the tricaprylin MVL formulation ($\Delta$). The rhu IGF-1 level in serum was determined by ELISA.

Male, Sprague-Dawley rats (weighing 250 to 300 g) were given subcutaneous injections of the multivesicular liposome formulation containing IGF-1 that were manufactured with either tricaprylin or tripalmitolein as the neutral lipid. The tricaprylin formulation demonstrated a higher peak level of plasma rhu IGF-1 and a short release duration compared to the formulation manufactured with tripalmitolein (FIG. 6). This result confirms the prediction of rapid release of multivesicular liposomes manufactured with tricaprylin based upon results of the in vitro release assay.

EXAMPLE 4

1. Manufacture

For manufacture of multivesicular liposomes containing rhu-insulin, the lipid combination solution contained (per ml chloroform): 11 mg DOPC, 2.3 mg DPPG, 8.7 mg cholesterol and either 2.4 mg (2.7 umol) triolein or 1.3 mg (2.7 umol) tricaprylin as indicated.

The first aqueous phase solution formulations contained 7.5% $^{14}C$-sucrose, 20 mM citric acid, 50 mM HCl and 5 mg/ml rhu-Insulin (E. coli, Sigma Chemical Co., St. Louis, Mo.). A first emulsion was made by high-speed mixing of 4 ml of the lipid combination solution with 4 ml of the aqueous phase solution at 9000 rpm for 8 minutes at 25–27° C. The emulsion was sheared into microdroplets (spherules) by addition of a solution to the mixing vessel of 20 ml 20 mM lysine, 4% glucose, and mixing at 3000 rpm for 1 min. The chloroform was removed from the microscopic droplets or spherules by transferring the suspension to a flask containing 30 ml of a solution of 20 mM lysine, 4% glucose at 37° C. in a gyrorotary water bath and flushing the surface of the suspension with nitrogen gas at a flow rate of 70 cubic feet per hour for 20 minutes to obtain the MVL particles in suspension.

The suspensions were diluted 1:4 with normal saline, and the particles were harvested by centrifugation at 800×g for 10 minutes. The supernatant solution was removed by aspiration, and the particles were washed twice by resuspension in fresh, normal saline solution and centrifugation. The final washed product was resuspended at 25% packed-particle volume per total volume and stored at 2–8° C. for subsequent studies.

2. In Vitro Release Rates

Figure 7:
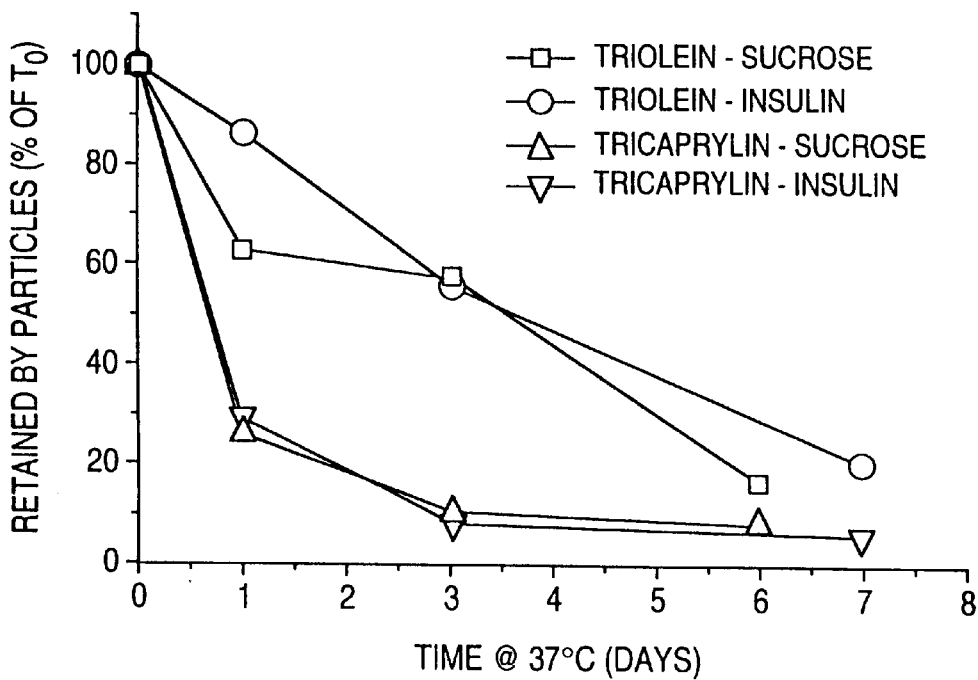
FIG. 7 is a graph showing the release of rhu insulin and coencapsulant $^{14}$C-sucrose from MVL manufactured with the neutral lipid, triolein or tricaprylin when incubated at 37° C. in saline solutions containing 60% human plasma. ($\square$) sucrose retained by triolein MVL formulation; ($\bigcirc$) insulin retained by triolein MVL formulation; ($\Delta$) sucrose retained by tricaprylin MVL formulation; and ($\nabla$) insulin retained by tricaprylin MVL formulation.

The "in vitro" release assay was performed by diluting 1 volume of stored suspension with 3.2 volumes of citrated, human plasma, and placing 0.6 ml of this suspension into microfuge tubes which were stoppered and incubated under dynamic conditions at 37° C. After 1, 3, 6, and 7 days, the tubes were centrifuged at 14,000×g×2 minutes, and the supernatant solution was transferred to another tube for bioassay. The pellet fractions of centrifuged samples were incubated in 1% NonIdet® NP-40 (CalBiochem, San Diego, Calif.), 50 mM trifluoroacetic acid for 10 minutes at 37° C. The $^{14}$C sucrose and insulin retained by the pellet fraction was determined, respectively, by scintillation counting and reverse phase HPLC using known methods. The results of these studies showed that the multivesicular liposomes manufactured with triolein as the neutral lipid released both sucrose and insulin in an equivalent and linear fashion, with nearly complete release in 7 days. By contrast, the formulation manufactured with tricaprylin retained only 20 to 25% of the encapsulated sucrose and insulin after only 1 day of incubation in plasma (FIG. 7).

EXAMPLE 5

1. Manufacture

For manufacture of multivesicular liposomes containing morphine, a GMP-validatable, scalable process was used. The neutral lipid component molar ratios of triolein to tricaprylin were 1:4 or 1:9. Control formulations contained triolein or tricaprylin as the sole neutral lipid. The lipid combination solution contained (per liter) 10.2 g DOPC, 2.0 g DPPG, 7.6 g cholesterol, 2.1 g to 1.1 g triglyceride depending on the molar ratio of triolein:tricaprylin, (molar ratio, 0.34:0.07:0.52:0.06).

The first aqueous phase solution contained (per liter) 21 g morphine sulfate pentahydrate, 0.01 N hydrochloric acid. A first emulsion was made by high-speed mixing of 0.62 l of lipid combination solution with 0.9 l of aqueous phase solution at 8000 rpm for 30 minutes at 25–27° C. The emulsion was sheared into microdroplets (spherules) by transferring to a second mixing vessel containing 15 liter 4 mM Lysine, 5.9% glucose solution; and mixing at 1250–1300 rpm for 1.5 min at 45° C. Chloroform was removed from spherules by sparging the suspension for 50 min at 45° C. in stepped intervals: 17 min at 15 l/min, 5 min at 40 l min, 28 min at 10 l/min. The MVL particles were thus obtained in suspension. The particles in the final suspension were concentrated and washed free of unencapsulated morphine by either cross-flow- or dia-filtration with 25 l of normal saline solution. The final washed product was stored at 2–8° C. for subsequent studies.

2. In Vitro Release Profiles

The in vitro release assays were performed by a 1:9 dilution of suspensions which contained 8 to 15 mg of encapsulated morphine sulfate per ml into human plasma. The suspensions were incubated at 37° C. under dynamic conditions. After 1, 2, 4, and 7 days, samples were diluted 1:4 with normal saline, the particles were sedimented by centrifugation at 800×g×10 min and the particle fraction was assayed to determine the amount of morphine retained by solubilization of the pellet fraction with 50% IPA and assay by UV spectrophotometry using known methods.

Figure 8:
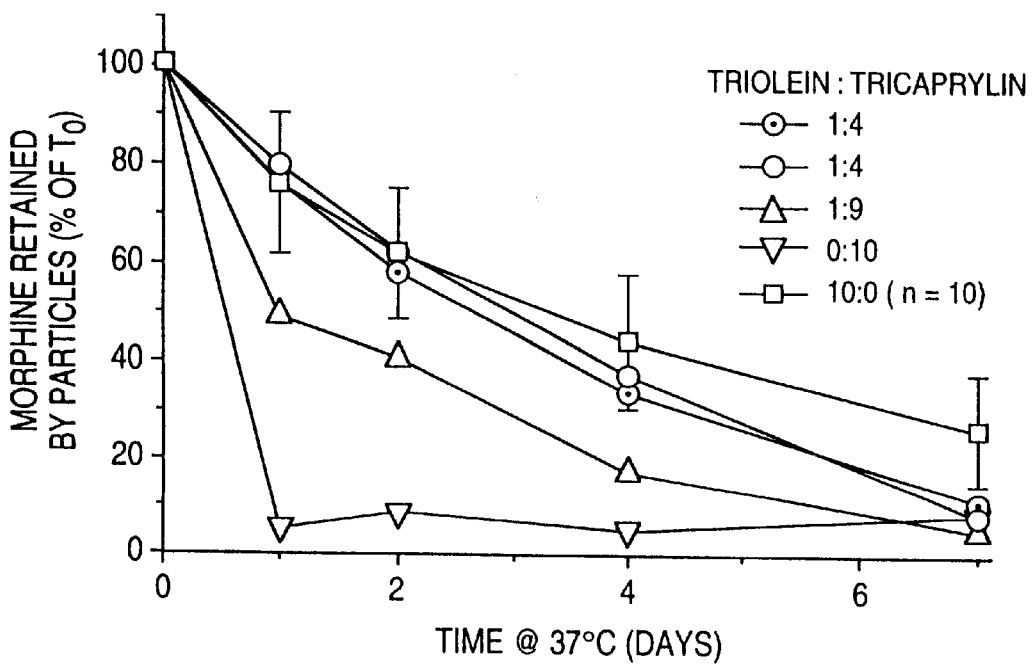
FIG. 8 is a graph comparing the release rates of morphine from MVL formulated with different molar ratios of triolein to tricaprylin as the neutral lipid when incubated at 37° C. in 60% human plasma in saline solution. ($\square$) 10:0, triolein:tricaprylin, 10 batches; ($\bigcirc\bigcirc$) 1:4, triolein:tricaprylin, 2 batches; ($\Delta$) 1:9, triolein:tricaprylin; ($\nabla$) 0:10, triolein:tricaprylin.

FIG. 8 shows the release rate profile of morphine release for these formulations into human plasma. As shown in earlier examples, as the ratio of the triolein to tricaprylin increases, the rate and extent of morphine release decreases.

3. In Vivo Pharmacokinetics

The in vivo release of the multivesicular liposomes containing morphine manufactured with triolein and tricaprylin alone or in combination was evaluated in the Beagle dog using an epidural injection, pharmacokinetic model. In these studies the level of morphine released from the liposomal formulation injected at a epidural site was determined in the plasma and at an adjacent intrathecal site (CSF, cerebral spinal fluid) separated from the epidural site by the spinal meningeal membrane. Only the CSF results are shown (FIG. 9).

Figure 9:
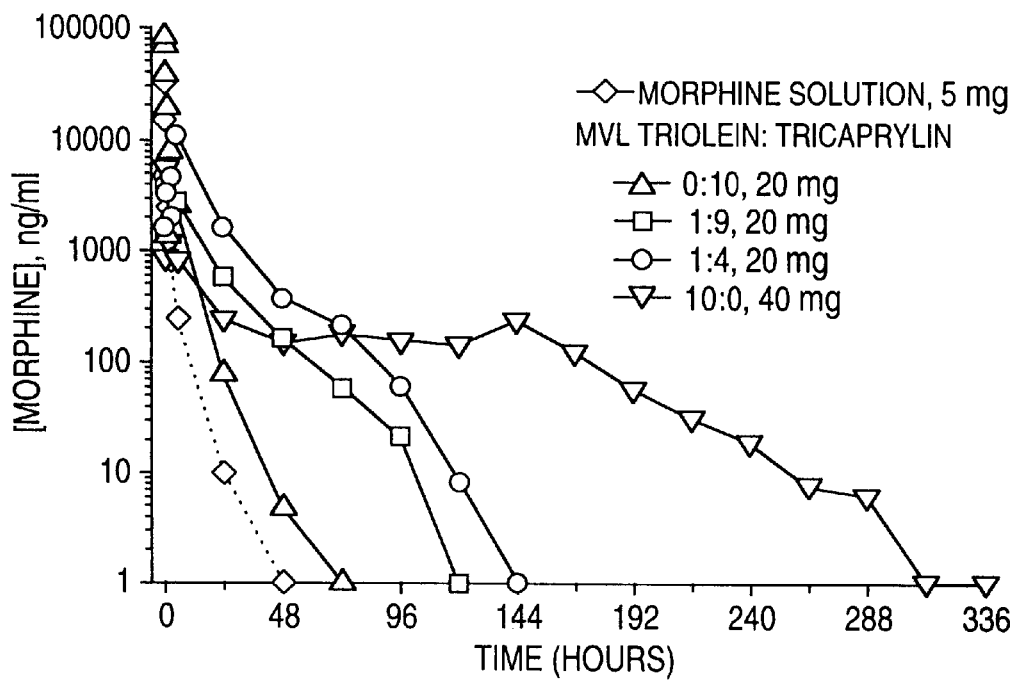
FIG. 9 shows results of a pharmacokinetic study of morphine MVL formulations manufactured with different molar ratios of triolein to tricaprylin and injected into the epidural space of Beagle dogs. Morphine release by the MVL was determined by measuring the level of morphine in the adjacent, dura membrane-separated, cerebral spinal fluid. ($\diamond$) 5 mg morphine (sulfate) in saline solution; ($\nabla$) 40 mg of morphine in the 10:0, triolein:tricaprylin MVL formulation; ($\bigcirc$) 20 mg of morphine in the 1:4, triolein:tricaprylin MVL formulation; ($\square$) 20 mg of morphine in the 1:9, triolein:tricaprylin MVL formulation; and ($\Delta$) 20 mg of morphine in the 0:10, triolein:tricaprylin MVL formulation.

A correlation is found between the in vitro release results summarized in FIG. 8 and the release rate profiles observed in the dog model (FIG. 9). The in vivo tricaprylin-containing formulation releases very rapidly, with nearly complete release in 24 hours. The Mean Residence Time (MRT) for the 100% tricaprylin formulation was similar to that for injection of unencapsulated morphine, i.e., 2.3 h vs. 1.6 h. The inclusion of a small amount of triolein during manufacturing, i.e., 1:9 or 1:4 triolein:tricaprylin molar ratio slows the release rate, extending the release duration over 4 to 5 days, with MRTs of 13.2 h and 15.3 h, respectively. The tricaprylin containing formulations all release more rapidly than the formulation using triolein as the only neutral lipid, which had a MRT of 69 h in this model.

4. Storage Stability

Figure 10:
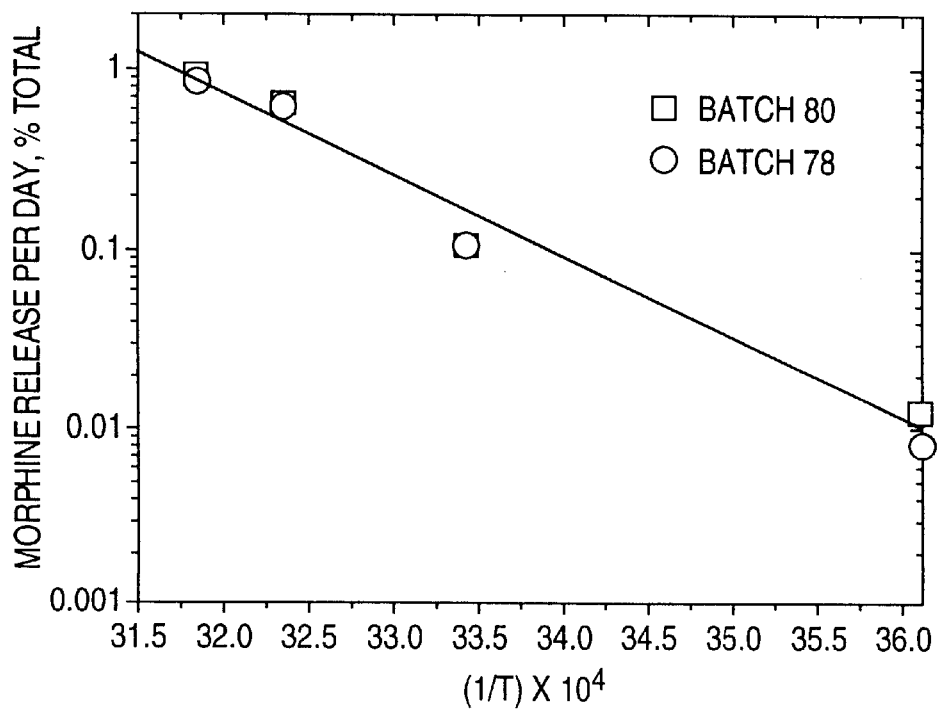
FIG. 10 is a graph summarizing in an Arrhenius STOPPED HERE transformation the results of a study determining the effect of storage temperature on release rate of morphine from 2 batches of the 1:9, triolein:tricaprylin MVL formulation. The MVL were stored in normal saline solution at 4° C., 2° C., 37° C., and 41° C. The ordinate is the rate of morphine release from MVL expressed in terms of amount released per day as a percentage of total amount of morphine in the MVL suspension; the abscissa is 1/storage temperature×$10^4$ (°K)$^{-1}$.

The step-wise alteration in the neutral lipid composition of the MVL to provide a family of formulations with step-wise increase in the release rate profiles of bioactive compound does not seem to compromise the storage stability of the formulations provided that the formulations are stored near or above the melting point of the neutral lipid combination. Batches of the 10:90 triolein:tricaprylin morphine MVL formulation, described above and which release rapidly both in vitro and in vivo, were evaluated for dependence of the release rate on temperature of storage. The MVL suspensions in saline storage solution were incubated at the normal storage temperature, 2–8° C. (4° C. nominal) and at elevated temperatures, 26, 37, and 41° C. The results of these studies are shown in FIG. 10, an Arrhenius plot, which plots the logarithm of the release rate against 1/Temperature (°K). The slope of the plot appears to be continuous. The release rate profile at high temperature supports the observation that the MVL stored in saline solution at 2–8° C. have a very slow release (about 1% of the encapsulated morphine per 100 days) and therefore can be expected to have a shelf-life in excess of a year if a criteria of 5 or 10% release of encapsulated material is the limit for shelf-life. Further, it is also evident that a physiological matrix such as plasma (FIG. 9) or the in vivo environment of the epidural space (FIG. 9) greatly accelerates the release when compared to the release in saline solution at 37° C., i.e., 50% of the encapsulated morphine released per day, versus less than 1% of encapsulated morphine per day in the latter.

EXAMPLE 6

Cytosine Arabinoside

1. Manufacture

Multivesicular liposomes containing cytosine arabinoside (AraC) were manufactured with various substitutions for the phosphatidylcholine component of the lipid organic phase solution. The substitutions were performed to determine the effect on the release rate profile of changing the acyl component in the major phospholipid in a MVL formulation containing either triolein or tricaprylin as the neutral lipid.

In this first example, DOPC is used to demonstrate that the release rate in a physiological medium from MVL formulations containing AraC/HCl in the aqueous phase can be modified by adjusting the triolein to tricaprylin ratio. The lipid combinations contained (per 1200 ml) 122.4 ml DOPC at 100 mg/ml, 2.4 g DPPG, 9.12 g cholesterol, 2.5 g triolein or 1.3 g tricaprylin, or a mixture thereof yielding a molar ratio of triolein to tricaprylin of 1:4, 1:9, 1:18, or 1:27.

The first aqueous phase solution contained 20 mg/ml cytosine arabinoside, 0.1 N Hcl. A first emulsion was made by high speed mixing of 10 ml lipid combination and 10 ml of first aqueous phase solution at 9000 rpm for 9 min. The emulsion was sheared into microdroplets by transfer of first emulsion to second mixing vessel containing 200 ml of 3.2% glucose, 40 mM lysine and mixing at 2100 rpm for 2.5 minutes. The chloroform was removed by transferring suspension to two, 1-liter flasks and flushing at 70 cfh. The final suspension was diluted 1:2 with saline and particles collected by centrifugation at 800×g×10 min washed 3 times, resuspended to 33% lipocrit, and then adjusted to 10 mg/ml.

2. In Vitro Release into Human Plasma

The in vitro release rate profiles of the cytosine arabinoside (AraC) MVL formulations were obtained by dilution of the suspension 1:9 into human plasma and incubation of samples at 37° C. under dynamic conditions. At time points of 1, 2, 4, and 7 days, 1.2 ml of saline was added to triplicate 0.3 ml samples, and the particle fraction was collected by centrifugation at 16,000×g×2 min. The supernatant fraction was removed by aspiration, and the particle fraction was resuspended in 1 ml of 50% isopropyl alcohol, vortexed, incubated at 37° C. for 10 min, centrifuged and then 0.06 or 0.2 ml of the supernatant was added to 1.0 ml of 0.1 N HCl. Cytosine arabinoside was determined by U.V. samples at 280 nm.

Figure 11:
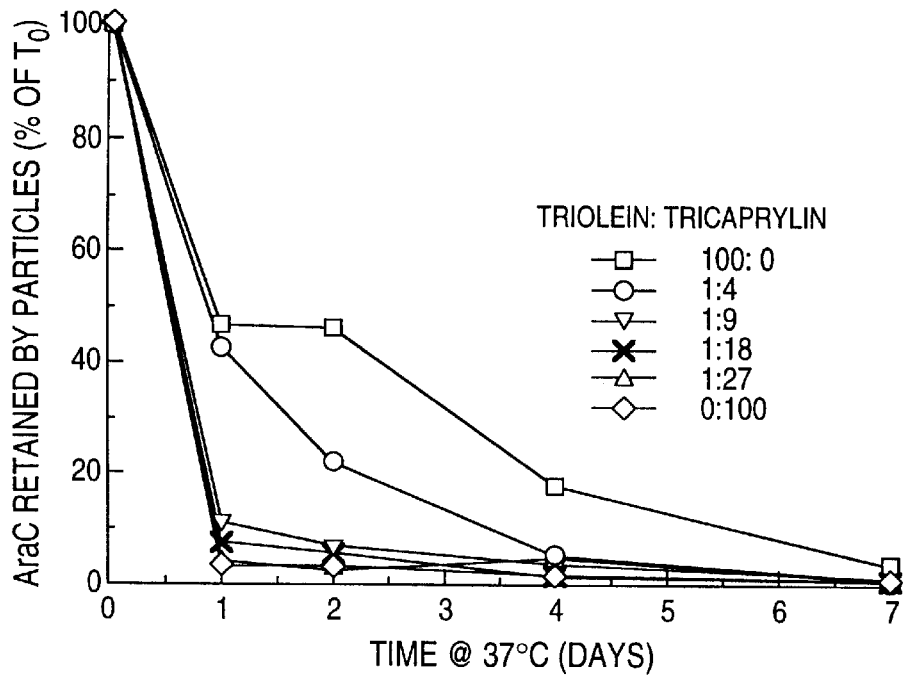
FIG. 11 is a graph showing cytosine arabinoside (AraC) retained in MVL incubated in human plasma at 37° C. The MVL formulations used as the neutral lipid component ($\square$) triolein only; ($\bigcirc$) 1:4, triolein:tricaprylin; ($\nabla$) 1:9, triolein:tricaprylin; (×) 1:18 triolein:tricaprylin; ($\Delta$) 1:27, triolein:tricaprylin; and ($\diamond$) tricaprylin only.

The in vitro release profiles measuring AraC retained by the formulations of multivesicular liposomes are shown in FIG. 11. Release from the formulation having only tricaprylin as the neutral lipid was rapid. As the ratio of tricaprylin to triolein used in the manufacture of the MVL formulation increases, the rate of release of cytosine arabinoside by the MVL incubated in plasma decreases. Thus, a family of release rate curves with predictably increasing release rates is created by incremental increases in the amount of triolein in the triolein to tricaprylin ratio.

EXAMPLE 7

Effect of Substitution of Higher Transition Temperature PhosphatidylCholines or Longer Chain Length for DOPC in Formulations Containing Tricaprylin The ranking in a family of in vitro release rate profiles (as obtained in Example 6) with the greater molar ratio of tricaprylin to triolein resulting in faster release both in vivo and in in vitro models (plasma at 37° C.), remains consistent when a phosphatidylcholine of higher phase transition temperature or of increased chain length is substituted for DOPC in the formulations of Example 6. In this example distearoylphosphatidylcholine (DSPC, mp 55° C.) was substituted for DOPC (mp 0° C.).

1. Manufacture

The manufacturing parameters were adjusted to accommodate the higher mp of DSPC by performing emulsification at 50° C. The manufacture of emulsions used for the DOPC control formulations was performed at ambient temperature. In addition, the HCl concentration of the first aqueous phase solution was increased 36% over that in Example 6.

The lipid combination solution contained (per liter) 10.2 g DOPC or 10.3 g DSPC, 2.1 g DPPG, 7.7 g cholesterol, and the triglyceride component was either 1.1 g tricaprylin or 2.1 g triolein (molar ratio of 0.34:0.07:0.52:0.06). Mixtures of triolein and tricaprylin were blended to provide the ratios of 1:4, 1:9, 1:18, 1:2 triolein to tricaprylin for use in the formulations.

The first aqueous phase contained (per ml) 20 mg cytosine arabinoside and 136 mM Hcl. An emulsion was made by high-speed mixing of 10 ml of the lipid combination solution with 10 ml of the aqueous phase solution using a 2 cm diameter blade in a stainless steel vessel at 9000 rpm for 8 minutes at room temperature (for formulations with DOPC) or 55° C. (for formulations with DSPC). The emulsion was sheared into microdroplets by transfer into a 400 ml glass Mason jar containing 200 ml of 5% glucose and 40 mM lysine and, using a 4 cm diameter blade, mixing at 4000 rpm for 1.5 minutes at the same temperature as used for the first emulsification. Chloroform was removed by placing the container in a 37° C. gyrorotary water bath and flushing the surface of the suspension with nitrogen gas at a flow rate of 70 cfh for 20 minutes.

The suspensions were diluted 1:4 with normal saline and the particles were collected by centrifugation at 800×g for 10 minutes at room temperature. The supernatant was removed by aspiration, and then the particles were washed twice by resuspension in normal saline solution and centrifugation. The final washed pellet was resuspended in normal saline solution and adjusted to 10 mg/ml of cytosine arabinoside.

2. In Vitro Release Profiles

Figure 12:
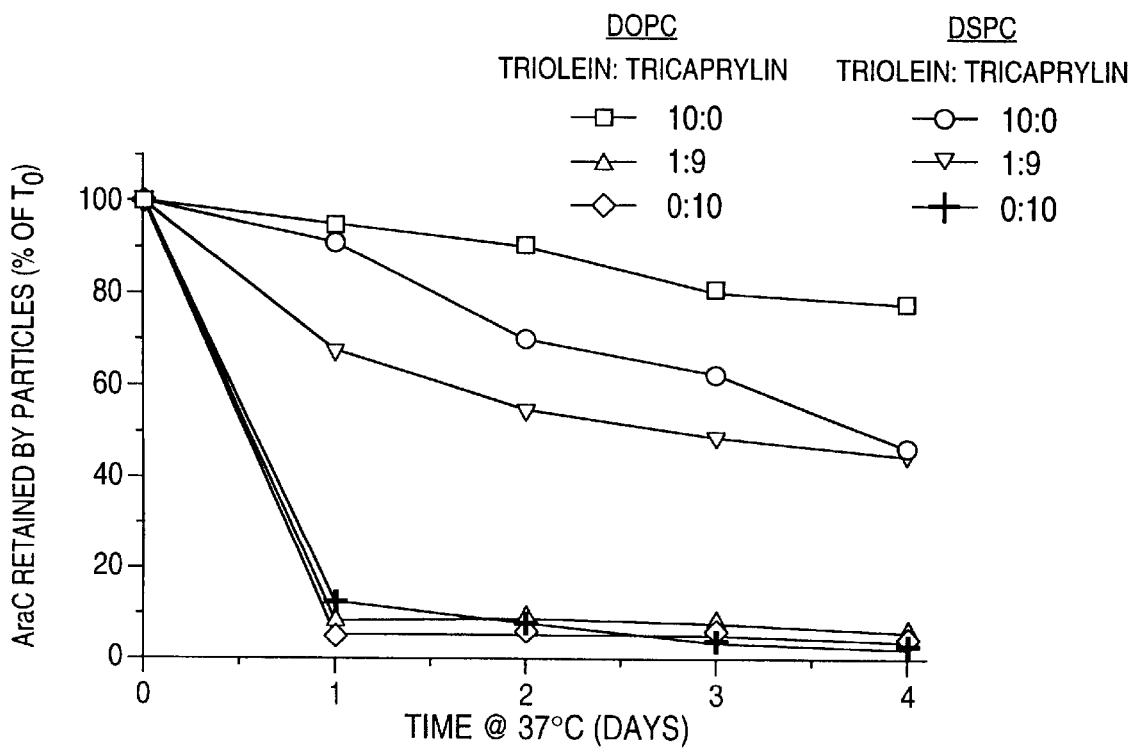
FIG. 12 is a graph showing the effect the neutral lipid ratio on release of cytosine arabinoside from MVL incubated in human plasma at 37° C. when the MVL were formulated with the major phospholipid component, DOPC, replaced with DSPC. The formulations were ($\square$) DOPC and triolein only; ($\Delta$) DOPC 1:9, triolein:tricaprylin; ($\diamond$) DOPC and tricaprylin only; ($\bigcirc$) DSPC and triolein only; ($\nabla$) DSPC 1:9, triolein:tricaprylin; and (+) DSPC and tricaprylin only.

The in vitro release assay of AraC from the MVLs was performed in human plasma as described in Example 6 above. As shown in FIG. 12, in MVL in which the higher melting point DSPC was substituted for DOPC, a family of graded release rate profiles was obtained by varying the molar ratio of tricaprylin to triolein, with the faster release formulations containing a higher molar ratio of tricaprylin to triolein. As has been shown previously for other formulations of MVL, an increase in hydrochloric acid concentration in the aqueous phase solution (as compared with that contained in the MVL of Example 6) can slow the release of the active substance in vitro.

EXAMPLE 8

Sucrose

1. Manufacture

In this example, the effect of tricaprylin on the release rate was tested for formulations containing 4% sucrose as the active agent in formulations having dieucrylphosphatidylcholine (DEPC, mp <0° C.), a 22 carbon chain length phosphatidylcholine, substituted for dioleolyphosphatidylcholine (DOPC, mp <0° C.), a 18 carbon chain length phosphatidylcholine.

The lipid solution contained (per liter) either 10.2 g DOPC or 11.0 g DEPC and 2.1 g DPPG, 7.7 g cholesterol, and the triglyceride component was either 1.1 g tricaprylin or 2.1 g triolein (molar ratio of 0.34:0.07:0.52:0.06). For mixtures of the neutral lipid, triolein- and tricaprylin-containing lipid combinations were blended to provide these triolein to tricaprylin molar ratios.

The first aqueous phase contained 4% Sucrose (Spectrum USP/NF, Los Angeles, Calif.) and was spiked with 40 uL of $^{14}C$ sucrose. A first emulsion was made by high-speed mixing of 5 ml of the lipid combination solution with 5 ml of the aqueous phase solution using a 2 cm diameter blade in a stainless steel vessel at 9000 rpm for 10 minutes at room temperature. The emulsion was sheared into microdroplets by transfer to a 400 ml glass Mason jar containing 200 ml of 4% glucose and 4 mM lysine for 2 minutes, using a 4 cm diameter blade and mixing at 3500 rpm. Chloroform was removed from the droplets by transferring the suspension to a 1 liter culture flask placed in 37° C. gyrorotary water bath and flushing the surface of the suspension with nitrogen gas at a flow rate of 70 cfh for 20 minutes.

The particle suspensions were diluted 1:2 with normal saline, and the particles were collected by centrifugation at 800×g for 10 minutes at room temperature. The supernatant was removed by aspiration, and the particles were washed twice by resuspension in normal saline solution and centrifugation. The final, washed particle pellet was resuspended in normal saline solution and adjusted to approximately 33% lipocrit.

2. In Vitro Plasma Release Studies

For in vitro, plasma release studies, the suspensions were diluted 1:10 in human plasma with 0.1% sodium azide. Triplicate aliquots of 300 uL were incubated in 1.5 ml screw-top Eppendorf tubes and harvested on days 0, 1, 2, 3, and 4. Samples were harvested by pulling tubes from the incubator at random, labeling the tube with day of pull, diluting the contents with 1.2 ml of normal saline solution, and centrifuging at 27,000×g for 5 minutes in a microfuge. The supernatant was carefully aspirated away from the particle pellet. The pellet fraction was resuspended in 1 ml of 50% IPA by vortexing, incubating at 37° C. for 10 minutes, and then vortexing. A 50 ul sample was then diluted with 3 ml of scintillation fluid in a scintillation vial, the vial was shaken vigorously and sucrose was determined by scintillation counting.

Figure 13:
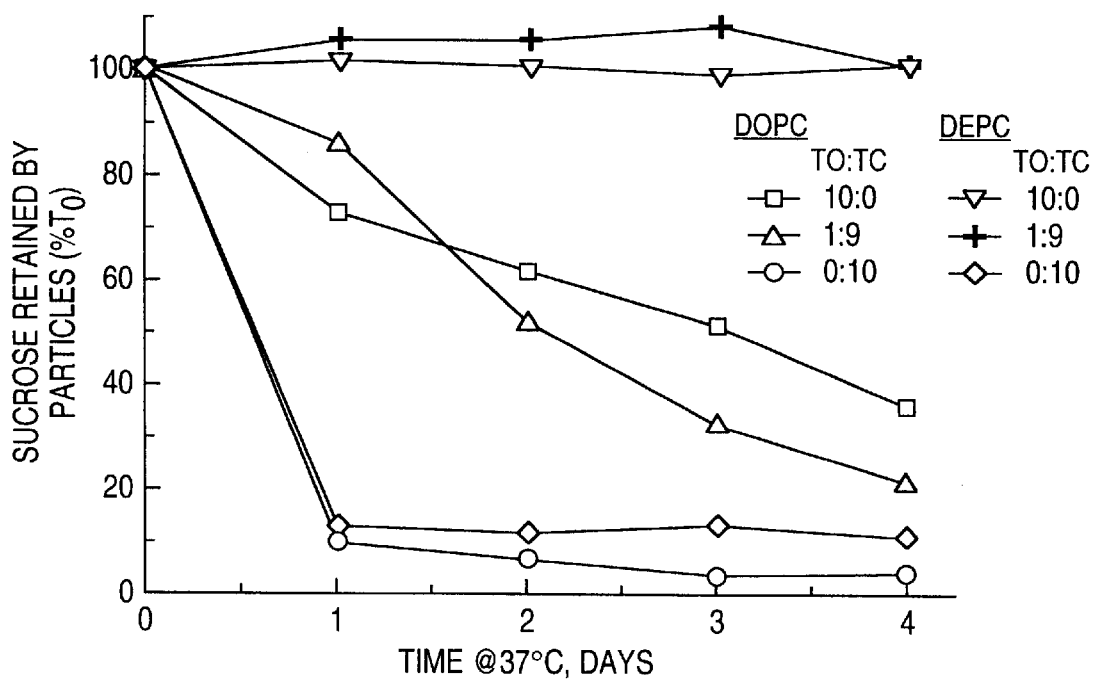
FIG. 13 is a graph showing the effect of the neutral lipid ratio on release of 14C-sucrose from MVL incubated in human plasma at 37° C. when the MVL were formulated with the major phopholipid component, DOPC, replaced with DEPC. The DOPC formulations were ($\square$) triolein only; ($\Delta$) 1:9, triolein:tricaprylin; and ($\bigcirc$) tricaprylin only. The DSPC formulations were ($\nabla$) triolein only; (+) 1:9, triolein:tricaprylin; and ($\diamond$) tricaprylin only.

As can be seen from the data contained in FIG. 13, the formulation containing only tricaprylin released all encapsulated sucrose within one day when incubated in plasma. The ratio of triolein: tricaprylin of 1:18 was required to achieve an intermediate rate of release for an MVL formulation with this aqueous phase when DEPC replaced DOPC.

EXAMPLE 9

In this example, tricaproin (C6) was substituted for tricaprylin (C8) as a release rate modifying neutral lipid.

1. Manufacture

The lipid combination solution contained (per liter) a combination of 10.2 g, 2.1 g DPPG, 7.7 g cholesterol, and the triglyceride component was either 0.9 g tricaproin or 2.1 g triolein (molar ratio of 0.34:0.07:0.52:0.06). Mixtures of the lipid solutions containing triolein and tricaproin, were blended to provide lipid solutions containing molar ratios of triolein to caproin of 1:4, 1:9 and 1:18. These formulations were manufactured and tested as described in Example 8.

The first aqueous phase contained 4% Sucrose (Spectrum USP/NF) and was spiked with 40 uL of $^{14}$C Sucrose (ICN lot#54661027). A first emulsion was made by high-speed mixing of 5 ml of the lipid combination solution with 5 ml of the aqueous phase solution using a 2 cm diameter blade in a stainless steel vessel at 9000 rpm for 10 minutes at room temperature. The second emulsification was performed in a 400 ml glass Mason jar containing 200 ml of 4% glucose and 4 mM lysine, using a 4 cm diameter blade and mixing at 3500 rpm for 2 minutes. Chloroform was removed by transferring the contents of the jar to a 1 liter culture flask placed in 37° C. gyrorotary water bath and flushing the surface of the suspension with nitrogen gas at a flow rate of 70 cfh for 20 minutes.

The suspensions were diluted 1:2 with normal saline, and the particles were harvested by centrifugation at 800×g for 10 minutes at room temperature. The supernatant was removed by aspiration, and the particles were washed twice by resuspension in normal saline solution and centrifugation. The final washed pellet was resuspended in normal saline solution and adjusted to approximately 33% lipocrit wherein lipocrit in percent is the volume occupied by the liposomes divided by the total volume of the liposome suspension multiplied by one hundred. The yield for each variation in the neutral lipid was greater than 50%. Following manufacture the free sucrose concentration at 33% lipocrit was approximately 3% of the total sucrose concentration.

2. In Vitro Release Profiles

For in vitro plasma release studies, the suspensions were diluted 1:10 in human plasma. Triplicate aliquots of 300 uL were incubated dynamically in 1.5 ml screw-top Eppendorf tubes and harvested on days 0,1,2,3, and 4. Samples were harvested by pulling tubes from the incubator at random, labeling the tube with the day of the pull, diluting the contents with 1.2 ml of normal saline solution, and centrifuging at 27,000×g for 5 minutes in microfuge. The supernatant was carefully aspirated away from the pellet. The pellet fraction was resuspended in 1 ml of 50% IPA by vortexing, incubating at 37° C. for 10 minutes, and then vortexing again. A 50 ul sample was then diluted with 3 ml of scintillation fluid in a scintillation vial, the vial was shaken vigorously, and 14C-sucrose radioactivity was determined by scintillation counting.

As shown in FIG. 14, the substitution of tricaproin for tricaprylin in mixtures containing triolein as a release rate modifying neutral lipid combination results in formulations having a graded family of release rates for various triolein:tricaproin molar ratios. The greater the molar ratio of tricaproin to triolein, the more rapid the release of sucrose. There is a distinguishing difference between tricaproin and tricaprylin containing formations. With this aqueous phase, i.e., containing sucrose as the encapsulated active agent, the multivesicular particles manufactured using only tricaproin underwent a physical transformation and released their contents within 5 minutes of dilution into human plasma at room temperature. Dilution into saline solution containing 0.5% bovine serum albumin had the same effect. By contrast, the formulations containing only tricaprylin as the neutral lipid generally required 12 or more hours of incubation in plasma at 37° C. for complete release of the active agent. Despite the instability of the tricaproin only formulations in human plasma or saline at room temperature. The formulations were stable during storage at 2–8° C. in saline for at least a week.

EXAMPLE 10

Antisense Oligonucleotides

This example illustrates use of the method of the invention to encapsulate antisense oligonucleotides.

1. Manufacture

The first aqueous phase solution contained (per ml) 5, 10 or 20 mg of an IL-6 antisense oligonucleotide (donated by Leu Neckers, NIH, Bethesda, Md.), which in some studies was biotinylated, and 5% mannitol.

Hydrochloric acid (0.1 ml of 1 N) was added to a vial containing 1 ml of the lipid combination of Example 1 and the combination was emulsified by fixing the capped vial in a horizontal configuration to the head of a vortex mixer (Scientific Products) and shaking at 2400 oscillations/min for 1 minute. The remainder of the first aqueous phase solution (0.9 ml 5% mannitol containing 10 mg antisense oligonucleotide) was added to the vial, and emulsification was continued for 5 minutes.

The final emulsion (2 ml) was divided and transferred to two vials containing 2.5 ml 3.2% glucose, and 40 mM lysine. The emulsion was dispersed into microscopic droplets by fixing the capped vial in a horizontal configuration to the head of a vortex mixer and shaking for 3 seconds at approximately 1200 rpm. The contents of the vial were transferred to a flask containing 5 ml of 3.2% glucose, 40 mM lysine, and the chloroform was removed from the microscopic droplets or spherules by transferring the flask to a 37° C. gyrorotary water bath, and flushing the surface of the suspension with nitrogen gas at a flow rate of 15 cubic feet per hour for 10 minutes.

The suspensions were diluted 1:4 with normal saline and the particles were harvested by centrifugation at 800×g for 10 minutes. The supernatant solution was removed by aspiration, and the particles were washed twice by resuspension in fresh, normal saline solution and centrifugation. The final washed product was resuspended at 25% packed-particle volume per total volume and stored at 2–8° C. for subsequent studies.

The recovery of encapsulated oligonucleotide was determined by diluting a sample of the suspension 1:1 with 0.1% SDS, incubating the sample in a boiling water bath for 2 minutes, and then diluting the sample (typically 1/20) into 0.1 N NaOH for determination of UV absorption using a wavelength scan from 320 to 212 nmeters. The concentration of oligonucleotide in the sample was calculated by subtracting the measured A320 absorbance value from the A257 absorbance value. A sample of the first aqueous phase solution served as the standard, 17.6 (A257-1 cm) units per mg/ml.

2. In Vitro Release Profiles

The in vitro release characteristics of multivesicular particles containing oligonucleotides were determined by measuring the amount of oligonucleotide remaining with particle fraction when incubated at 37° C. in rat cerebral spinal fluid (CSF). Samples stored in normal saline were resuspended in the storage solution, and centrifuged at 750×g for 10 minutes. The saline supernatant solution was removed by aspiration, and the particles were resuspended in rat CSF to concentrations of 0.25 to 0.5 mg of the oligonucleotide per ml of CSF. The samples were incubated at 37° C. under static conditions. After 0, 1, 2, 3, and 7 days, samples of the particle/CSF suspensions were removed, diluted 10-fold in saline, centrifuged, and the supernatant was aspirated away from the particle fraction. The particle fraction was incubated in 0.1% SDS and diluted with 0.1 N NaOH, and a UV absorbance spectrum of the oligonucleotide was obtained over 340 to 210 nmeter range. The amount of oligonucleotide retained by the particle fraction was determined as above.

As shown in FIG. 15, the tricaprylin formulation did not release in vitro more rapidly, but rather had a greater overall release; the triolein-containing formulation stopped releasing the drug in rut CSF after about 2.5 days as compared with continued release by the tricaprylin-containing formulation.

3. In Vivo Pharmacokinetics

When the antisense MVL formulations manufactured with tricaprylin as the neutral lipid were tested in vivo by intrathecal injection in rats and samples of the CSF subsequently taken were examined microscopically, no particles were evident in CSF after two days. The MVL particles manufactured with triolein were evident at two days but had a "shrunken" appearance. There was no evidence of free, native oligonucleotide by a 3'-end labeling assay.

To improve the sensitivity of the in vivo assay for oligonucleotide concentration in CSF, the oligonucleotide was biotinylated and the biotinylated oligonucleotide was formulated as described above in MVL using either triolein or tricaprylin as the neutral lipid. The recoveries of encapsulated biotinylated oligonucleotide were 78% for triolein and 82% for tricaprylin-containing MVL. When studied in vivo, biotinylated oligonucleotide, found free in the CSF released from the tricaprylin-containing liposomes was below the limit of detection after 2 days. Free, biotinylated oligonucleotide was present in the rat sample CSF 4 days after administration of the triolein-containing formulations at a concentration of approximately 0.5 uM (results not shown). The in vivo data are consistent with the tricaprylin MVL rapidly releasing antisense oligonucleotide in vivo, and the triolein formulation providing a more sustained release of the oligonucleotides.

EXAMPLE 11

Plasmid-Containing MVL

1. Manufacture

For manufacture of multivesicular liposomes encapsulating the E. coli PBR322 plasmid, the lipid combination solution contained (per liter) 10.4 g DOPC, 2.1 g DPPG, 7.7 g cholesterol, 2.16 g triolein (mw 885.40) or 1.15 g tricaprylin (mw 470.7) (DOPC:DPPG:Cholesterol:triglyceride molar ratio, 0.34:0.07:0.52:0.06).

The first aqueous phase solution contained (per liter) 42 g $^{14}$C-sucrose (0.6 uCi per ml) 100 mmol lysine, 84 mmol hydrochloric acid, pH 7.4 and 20 ug/ml PBR322 plasmid (Promega, Madison Wis.). A first emulsion was made by high-speed mixing of 3 ml of lipid combination solution with 3 ml of aqueous phase solution at 9000 rpm for 9 minutes at 25–27° C. The emulsion was sheared into microdroplets (spherules) by addition of 20 ml of a 20 mM lysine, 4% glucose solution to the mixing vessel and further mixing at 4000 rpm for 2 min. The chloroform was removed from the microscopic droplets or spherules by transferring the suspension to a flask containing 30 ml of 20 mM lysine, 4% glucose solution at 37° C. in a gyrorotary water bath, and flushing the surface of the suspension with nitrogen gas at a flow rate of 70 liter per hr. for 20 minutes to form the MVL.

The MVL suspensions were diluted 1:4 with normal saline, and the particles were harvested by centrifugation at 800×g for 10 minutes. The supernatant solution was removed by aspiration and the particles were washed twice by resuspension in fresh, normal saline solution and centrifugation. The final washed product was resuspended to 25% packed-particle volume per total volume, and stored at 2–8° C. for subsequent studies.

2. In Vitro Release Profile

The in vitro release assays were performed by a 1:2.5 dilution of suspensions which contained the multivesicular liposomes encapsulating PBR322 plasmid and $^{14}$C-sucrose into human plasma. Previous studies had established that $^{14}$C-sucrose release was an adequate surrogate for estimating the release of the PBR322 plasmid from the MVL. The suspensions were incubated at 37° C. under static conditions. At times of 0, 1, 2, 3, 6, 10, and 17 days, samples were diluted 1:4 with normal saline, particles were sedimented by centrifugation at 800×g×10 min, and the particle fraction was assayed by dissolving samples in a scintillation counting solution and performing scintillation counting of the amount of $^{14}$C-sucrose retained by the particle fraction.

The results of this study shown in FIG. 16 indicate the PBR322 plasmid formulation using triolein as the neutral lipid was stable under simulated in vivo conditions and released about 30% of the encapsulated $^{14}$C-sucrose over a span of 17 days; whereas, the tricaprylin-formulated particles rapidly released their contents upon contact with human plasma at 37° C.

EXAMPLE 12

In the following example sucrose and lysine-HCl used as excipients in the PBR322 plasmid formulation were encapsulated without additional active agent to yield an "excipient only" family of graded, sucrose release formulations using tripalmitolein:tricaprylin molar ratios as the neutral lipid.

1. Manufacture

For manufacture of multivesicular liposomes encapsulating only sucrose-lysine HCl, the lipid combination solution contained (per liter) 10.4 g DOPC, 2.1 g DPPG, 7.7 g cholesterol, 1.9 g to 1.0 g triglyceride depending on the molar ratio of tripalmitolein (mw 801, C16:1 9C):tricaprylin to yield a DOPC:DPPG:cholesterol:triglyceride molar ratio of 0.34:0.07:0.52:0.06. The molar ratios of tripalmitolein to tricaprylin prepared in the formulations of this example were 0:1, 1:0, 1:9, 1:4, 1:2, and 1:1.

The first aqueous phase solution contained (per liter) 42 g $^{14}$C-sucrose (1.0 µCi per ml), 100 mmol lysine, 90 mmol hydrochloric acid, pH 5.7. A first emulsion was made by high-speed mixing of 5 ml of lipid combination solution with 5 ml of aqueous phase solution at 9000 rpm for 9 minutes at 25–27° C. The emulsion was sheared into microdroplets (spherules) by addition of 20 ml of a 20 mM lysine, 4% glucose solution to the mixing vessel, and mixing at 5000 rpm for 1.5 min. The chloroform was removed from the microscopic droplets or spherules by transferring the suspension to a flask containing 30 ml of the 20 mM lysine, 4% glucose solution in a 37° C. gyrorotary water bath, and flushing the surface of the suspension with nitrogen gas at a flow rate of 70 cubic feet per hr. for 20 minutes to obtain the multivesicular particles in suspension.

The suspensions were diluted 1:4 with normal saline, and the particles were harvested by centrifugation at 800×g for 10 minutes. The supernatant solution was removed by aspiration and the particles were washed twice by resuspension in fresh, normal saline solution and centrifugation. The final washed product was resuspended at 25% packed-particle volume per total volume and stored at 2–8° C. for subsequent studies.

2. In Vitro Release Profile

The "in vitro" release assays were performed by a 1:9 dilution into human plasma of suspensions which contained multivesicular liposome encapsulating $^{14}$C-sucrose. The suspensions were incubated at 37° C. under dynamic gentle mixing. At time points of 0, 1, 3, 5, 8, and 12 days, samples were diluted 1:4 with normal saline, the particles were sedimented by centrifugation at 800×g for 10 min, and the particle fraction was assayed by dissolving in scintillation counting solution and scintillation counting of the amount of $^{14}$C-sucrose retained in the particles. The results of these studies (FIG. 17) show that a 1:1 molar ratio of tripalmitolein to tricaprylin provided a somewhat slower release rate than tripalmitolein alone. A graded family of release rates was obtained having faster release by increasing the proportion of tricaprylin in the neutral lipid component.

EXAMPLE 13

Anesthetics

1. Tetracaine MVL Formulations

For manufacture of MVL encapsulating tetracaine, the lipid combination solution contained (per ml chloroform) 15.6 mg DOPC, 3.1 mg DPPG, 11.5 mg cholesterol, and 12.6 mg to 6.6 mg triglyceride depending on the molar ratio of triolein:tricaprylin. The lipophilicity of tetracaine was found to require that the concentration of lipid (68 umol/ml) in the lipid combination be increased 2 to 1.5 times higher to obtain satisfactory MVL formulations. The triglyceride was enriched as well; the molar ratio of DOPC:DPPG:cholesterol:triglyceride was 0.29:0.06:0.44:0.21. The molar ratios of triolein to tricaprylin prepared in the formulations of this example were 1:0; 1:10; 0.5:10; 0.2:10; 0.1:10; 0.05:10; and 0:1. The first aqueous phase solution for encapsulation of tetracaine contained (per ml) 15 mg of tetracaine phosphate and 200 mg of alpha-cyclodextrin polymer.

An aliquot of first aqueous phase solution (1 ml) was added to a vial containing 1 ml of the lipid combination and emulsified by fixing the capped vial in a horizontal configuration to the head of a vortex mixer (Scientific Products), and shaking at 2400 oscillations/min for 12 minutes.

The final emulsion (1 ml) was divided and transferred to two vials containing 2.5 ml of a solution of 3.2% glucose, 5 mM lysine. The emulsion was dispersed into microscopic droplets by fixing the capped vial in a horizontal configuration to the head of a vortex mixer and shaking for 3 seconds at a setting of 600–800 oscillations/min. The contents of the vial were transferred to a flask containing 50 ml of a solution of 3.2% glucose, 5 mM lysine, and the chloroform was removed from the microscopic droplets or spherules by transferring the flask to a 37° C. gyrorotary water bath, and flushing the surface of the suspension with nitrogen gas at a flow rate of one liter per min. for 20 minutes.

The suspensions were diluted 1:4 by volume with normal saline, and the particles were harvested by centrifugation at 800×g for 10 minutes. The supernatant solution was removed by aspiration, and the particles were washed twice by resuspension in fresh, normal saline solution and centrifugation.

2. In Vivo Pharmacokinetics

The in vivo release characteristics of the multivesicular particles were determined in BalbC mice (aged 7 to 8 weeks; weighing approximately 20 grams) by subcutaneous injection in the abdomen region (100 ul). At time points of 0, 5, and 24 hours after injection, mice were sacrificed, the subcutaneous tissue was harvested, homogenized, and extracted, and extracts were assayed by HPLC using UV detection for the amount of tetracaine retained.

The desired in vivo release duration for the tetracaine MVL was 24 hours. Formulations which contained triolein only as the neutral lipid were found to be stable in vivo and released over too long a duration.

By including tricaprylin in the neutral lipid component, formulations with shorter duration and more desirable pharmacokinetic profiles were obtained (FIG. 18). The desired 24 hour release duration for the anesthetic was provided by a formulation with a 1 triolein:100 tricaprylin ratio.

The Relationship Between Neutral Lipid Selection and Intended Storage Temperature As shown in the following examples, the melting point of the neutral lipid is an important consideration in selection of the rate-modifying neutral lipid. However, other factors must also be taken into account, for example, the composition of the first aqueous phase solution. The conclusion to these examples is that the freezing (melting or cloud) point of the neutral lipid or neutral lipid mixture should be above or near the storage temperature in order to assure storage stability. If formulations are stored at temperatures significantly lower than the freezing point of the neutral lipid or mixture thereof, the MVL particles undergo a physical, morphological transition, which results in loss of internal structure and release of encapsulated materials. This transition may occur within a few hours or over several days or weeks, depending on the composition of the first aqueous phase composition.

EXAMPLE 14

In the following example, MVLs were manufactured with either tricaprylin or tricaprin as the neutral lipid component. The freezing point of tricaprylin is 8° C. and that of tricaprin is 31° C. The first aqueous phase contained either cytosine arabinoside or morphine sulfate in 0.1 N HCl. Aliquots of the final product were stored in saline at 2–8, 25, 32, and 37° C. The release of encapsulated materials was determined over the time of storage.

1. Manufacture

For manufacture of MVLs, the lipid combination solution contained (per liter) 10.4 g DOPC, 2.1 g DPPG, 7.7 g cholesterol, and the triglyceride component was either 0.93 g tricaprylin (C8) or 1.1 g tricaprin (C10) (molar ratio, 0.34:0.07:0.52:0.06). The first aqueous phase solution contained either (per ml) 20 mg cytosine arabinoside in 0.1 N HCl or 20 mg morphine sulfate pentahydrate in 0.1 N HCl.

For formulations encapsulating cytosine arabinoside, the first emulsion was made by high-speed mixing of 10 ml of lipid combination solution with 10 ml of aqueous phase solution at 9000 rpm for 14 minutes at 25–27° C. with a high shear blade. For formulations encapsulating morphine, the first emulsion was made by high-speed mixing of 12.5 ml of the lipid combination solution with 7.5 ml of the aqueous phase solution at 9000 rpm for 14 minutes at 25–27° C. The first emulsions were sheared into microdroplets (spherules) by transfer to a mixing chamber containing 200 ml of 40 mM lysine, 3.2% glucose solution, and mixing at 2100 rpm for 2.5 min. The chloroform was removed from the microscopic droplets or spherules by transferring the suspension to a flask, placing the flask in 37° C. gyrorotary water bath, and flushing the surface of the suspension with nitrogen gas at a flow rate of 70 cfh for 20 minutes.

The suspensions were diluted 1:4 by volume with normal saline, and the particles were harvested by centrifugation at 800×g for 10 minutes at room temperature. The supernatant solution was removed by aspiration, and the particles were washed twice by resuspension in fresh, normal saline solution and centrifugation. The final washed product was resuspended at 33% packed-particle volume and stored.

The characterization of yields of encapsulated and free (supernatant) cytosine arabinoside and morphine from the tricaprylin and tricaprin MVL formulations was performed a few hours post-manufacture (Table 2). The yield of encapsulated cytosine arabinoside and morphine was acceptable, and the free (supernatant) concentrations of cytosine arabinoside and morphine were low for both the tricaprylin and tricaprin formulations.

TABLE 2

| First Aqueous Phase Active Agent | Neutral Lipid | Yield, % of Initial Active | Storage Concentration, mg/ml | Supernatant Concentration, mg/ml |
| --- | --- | --- | --- | --- |
| Cytosine Arabinoside | Tricaprylin | 42 | 7.0 | 0.3 |
|  | Tricaprin | 37 | 6.2 | 0.2 |
| Morphine Sulfate | Tricaprylin | 46 | 11.2 | 0.3 |
|  | Tricaprin | 36 | 8.9 | 0.2 |

2. Storage Release Profiles

The suspensions were stored at 2–8, 25, 32 or 37° C. At time points of 24, 48 and 200 hours the suspensions were centrifuged at 25,000×G for 2 minutes, and supernatant solutions were analyzed for content of cytosine arabinoside or morphine by 1:1 volume dilution with 50% isopropyl alcohol, vortexing, incubation at 37° C. for 10 min, and centrifugation. The supernatant samples were analyzed by dilution into 0.1 N HCl and the concentration of cytosine arabinoside was measured by absorbance determined at 280 nm, or dilution into 0.1 N NaOH, and the morphine concentration was measured by absorbance determined at 298 nm.

Figure 19C:
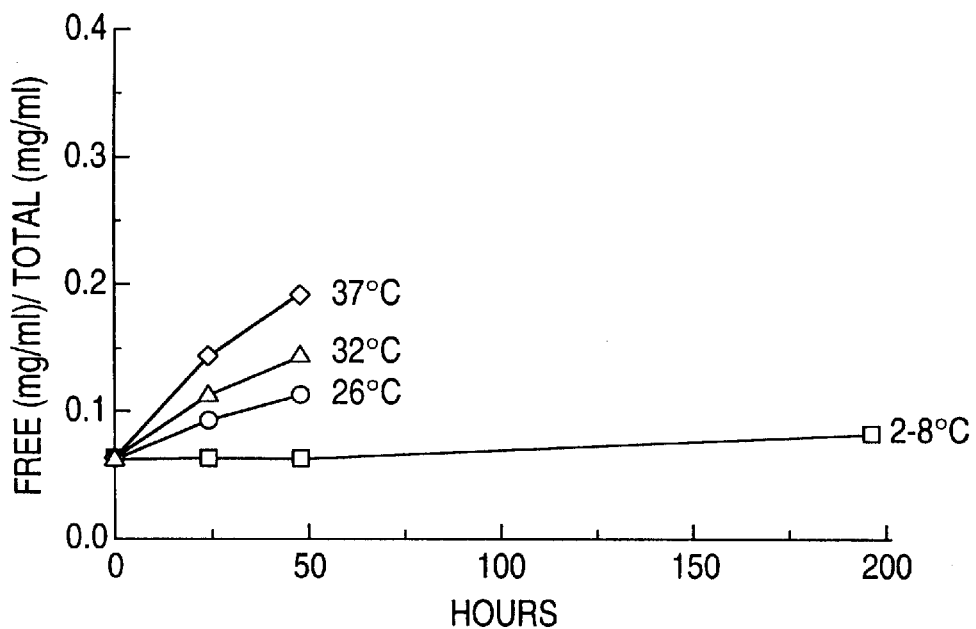

The results of these storage-temperature-effect studies are shown in FIGS. 19A–D. Release rates from the MVL containing tricaprylin (melting point 8° C.) are very slow at 2–8° C. Release rate increased with increasing storage temperature as would be expected as consistent with acceleration of release with elevation of temperature (FIGS. 19A and 19C). The AraC-MVL containing tricaprin (melting point 31° C.), however, released the active agent at a very fast rate when stored below the melting point of the triglyceride. With storage of the tricaprin MVL at higher temperatures 25° and 32°, the release rate decreased, but with storage at 37° again increased (FIG. 19B). In fact, the tricaprin-containing AraC-MVL particles stored below the melting point temperature of the neutral lipid tricaprin (31° C.), were completely destabilized and released the encapsulated morphine over a few hours (FIG. 19B).

The results for the storage study of cytosine arabinoside-containing MVL are shown in FIG. 20 by an Arrhenius plot. The tricaprylin MVL formulation showed an expected continuous linear relationship when log of the release rate is plotted versus temperature, suggesting that a single process is responsible for release. On the other hand, the plot of the data for the tricaprylin formulation was discontinuous, indicating that two processes are responsible for release in the temperature range studied. At higher temperatures above the freezing point of tricaprin, the slope was as expected, i.e., rates increased with increased temperature of storage. The second process, the melting point effect, is observed below the freezing point of tricaprin wherein, the apparent rate increased with decreasing temperature.

Figure 19D:
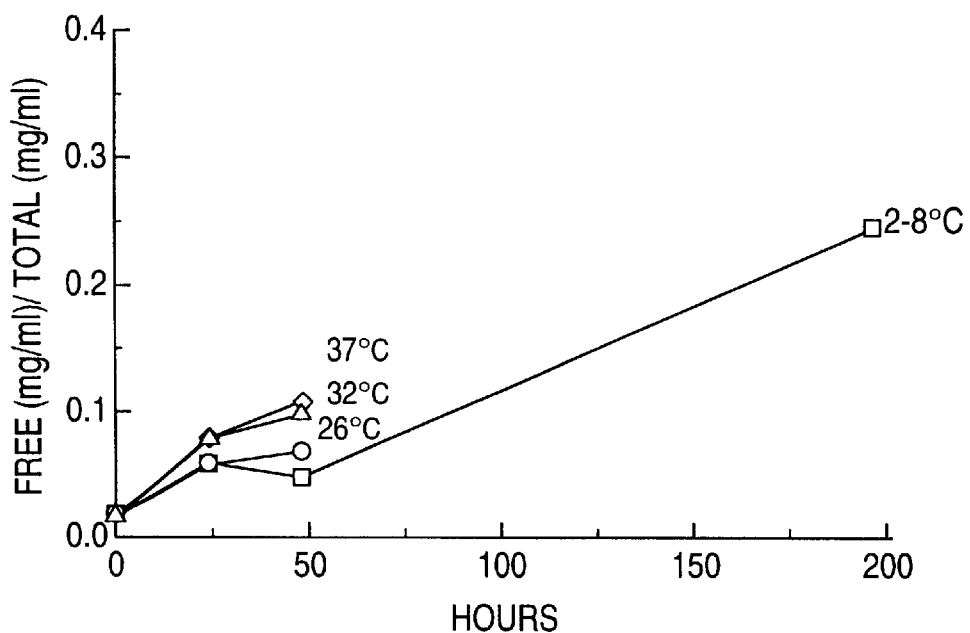

Again, comparison of the release rate profiles (19A–D) of particles having cytosine arabinoside encapsulated as a first aqueous phase component with particles having morphine sulfate encapsulated indicates that onset of the destabilizing effect caused by storage of formulations below the melting point of the neutral lipid, called herein "the melting point effect," is dependent on the composition of the first aqueous phase solution. Onset of the melting point effect of tricaprin MVL during storage was observed to be rapid with cytosine arabinoside-containing formulations, (FIG. 19B) but required several days for the morphine sulfate-containing formulations (FIG. 19D). Further, the results of these studies suggest that the further below the freezing point the formulation is stored, the more rapid the onset of the melting point effect.

EXAMPLE 15

In this example, the aqueous phase contained sucrose, cytosine arabinoside and 0.1 N HCl as an osmotic spacer. MVL were manufactured with triolein (mp 8° C.), tricaprin (mp 31° C.), or trilaurin (mp 46° C.) as the neutral lipid. The final product was stored at a temperature of 2–8° C., 22, or 37° C., and the release of encapsulated materials was recorded during the time of storage.

1. Manufacture

For manufacture of MVL encapsulating cytosine arabinoside with sucrose as an osmotic spacer in the presence of 0.1 N HCl, the lipid combination solution contained (per liter) 10.4 g DOPC, 2.1 g DPPG, 7.7 g cholesterol, and the triglyceride component was either 1.1 g tricaprin (C10), 1.3 g trilaurin (C12), or 1.7 g triolein (molar ratio of DOPC:DPPG:cholesterol:triglyceride was 0.34:0.07:0.52:0.06).

The first aqueous phase solution contained (per ml) 20 mg cytosine arabinoside and 51.3 mg sucrose in 0.1 N Hcl. A first emulsion was made by high-speed mixing of 3 ml of lipid combination solution with 3 ml of aqueous phase solution at 9000 rpm for 8 minutes at 25–27° C. The emulsion was sheared into microdroplets (spherules) by addition of 20 ml of a 20 mM lysine, 4% glucose solution to the mixing vessel and mixing at 5000 rpm for 1.5 min. The chloroform was removed from the microscopic droplets or spherules by transferring the suspension to a flask containing 70 ml of a 40 mM lysine, 3.2% glucose solution, placing the flask in 37 C. gyrorotary water bath and flushing the surface of the suspension with nitrogen gas at a flow rate of 70 cfh for 20 minutes to form the MVL particles in suspension.

The suspensions were diluted 1:4 by volume with normal saline, and the particles were harvested by centrifugation at 800×g for 10 minutes at room temperature. The supernatant solution was removed by aspiration, and the particles were washed twice by resuspension in fresh, normal saline solution and centrifugation. The final washed product was resuspended at 25% packed-particle volume per total value and stored at 2–8, 22, and 37° C. for 1 or 6 days (data not shown). The suspension and the suspension and the supernatant fraction obtained by centrifugation at 25,000×G 2 minutes were analyzed for content of cytosine arabinoside by 1:1 volume dilution with 50% isopropyl alcohol, vortexing, incubation at 37° C. for 10 min, and centrifugation. Then 0.06 or 0.2 ml of the sample was added to 1.0 ml of 0.1 N HCl, and cytosine arabinoside concentration was measured by absorbance determined at 280 nm.

TABLE 3

| Triglyceride Component | Storage Temp ° C. | Total AraC Encapsulated mg/ml | Supernatant Arac @ 24h mg/ml | Ratio of Supernatant to total (Sup/Total) |
|---|---|---|---|---|
| Triolein, mp 5° C. | 2–8 | 6.0 | 0.4 | 0.06 |
| | 22 | 5.6 | 0.3 | 0.05 |
| | 37 | 5.2 | 0.9 | 0.17 |
| Trilaurin, mp 46° C. | 2–8 | 3.0 | 2.5 | 0.82 |
| | 22 | 3.1 | 2.0 | 0.65 |
| | 37 | 3.0 | 2.3 | 0.78 |
| Tricaprin, mp 31° C. | 2–8 | 5.6 | 5.0 | 0.90 |
| | 22 | 5.4 | 4.8 | 0.90 |
| | 37 | 6.7 | 0.6 | 0.09 |

As shown by data in Table 3, the product yield of the MVL formulated using each of the neutral lipids was at least 3.0 mg/ml, an acceptable yield. Inspection of the particles with white light microscopy showed that the particles were spherical and multivesiculated in appearance immediately post-manufacture. However, within 24 hours of storage at temperatures below the melting point of the triglyceride, the particles changed in appearance. Associated with the change in appearance was significant loss of the encapsulated AraC to the storage solution (supernatant) as can be seen by the data in column 3 of Table 3. Noteworthy, the formulation manufactured with tricaprin (mp. 31° C.) did not change in appearance, or lose significant AraC when stored at 37° C.; whereas the formulation with trilaurin (mp 46° C.) did undergo a significant morphological change and loss of encapsulated active agent. Thus in formulating MVL for in vivo controlled and sustained delivery of the encapsulated active agent, the neutral lipid selected should usually have a melting point below or near the intended storage temperature. A preferred formulation would maintain a supernatant/total ratio of less than 0.10 during storage.

EXAMPLE 16

This example illustrates that certain aqueous phase solutions are interactive with the lipid layer membrane of MVLs and prevent freezing of the liposomes at storage temperatures below the melting point of the neutral lipid. In such cases, the morphological transition of the particles and loss of encapsulated materials associated with storage below the melting point of the neutral lipid may occur very slowly, or disappear. Instead the release of encapsulated materials is associated with activation by storage temperature increase.

1. Manufacture

For manufacture of MVL encapsulating rhu IGF with $^{14}$C-sucrose as the osmotic spacer and ammonium citrate as the buffer, the lipid combination solution contained (per liter) 10.4 g DOPC, 2.1 g DPPG, 7.7 g cholesterol, and the triglyceride component was 1.3 g tricaprin (mp 31° C., C10) (with the molar ratio of DOPC:DPPG:cholesterol:triglyceride was 0.34:0.07:0.52:0.06).

The first aqueous phase solution contained (per ml) 16 mg rhu IGF-1 (Chiron, Foster City, Calif.), 7% $^{14}$C-sucrose, and 20 mM ammonium citrate, pH 5. A first emulsion was made by high-speed mixing of 5 ml of lipid combination solution with 5 ml of aqueous phase solution at 9000 rpm for 9 minutes at 25–27° C. The emulsion was sheared into microdroplets (spherules) by addition of 30 ml of a 40 mM lysine, 4% glucose solution to the mixing vessel and mixing at 6000 rpm for 1 min. The chloroform was removed from the microscopic droplets or spherules by transferring the suspension to a flask containing 70 ml of a 40 mM lysine, 3.2% glucose solution, placing the flask in a gyrorotary water bath at 37° C., and flushing the surface of the suspension with nitrogen gas at a flow rate of 70 cfh for 20 minutes to obtain the MVL particles.

The suspensions were diluted 1:4 with normal saline and the particles were harvested by centrifugation at 800×g for 10 minutes at room temperature. The supernatant solution was removed by aspiration, and the particles were washed twice by resuspension in fresh, normal saline solution and centrifugation.

2. In Vitro Release Rates

The final washed product was resuspended at 25% packed-particle volume per total volume and stored at temperatures of 2–8, 25, 32, and 37° C. for 24 or 48 hours. The pellet and supernatant fraction from the centrifugation at 25,000×G for 2 minutes was assayed for content of IGF-1 (pellet fraction only) and $^{14}$C-sucrose.

TABLE 4

| Temperature, | Retained @ 24 hours | | Retained @ 48 hours | |
|---|---|---|---|---|
| ° C. | $^{14}$C-Sucrose | IGF-1 | $^{14}$C-Sucrose | IGF-1 |
| 2–8 | 1.00 | 1.00 | 0.98 | 0.98 |
| 25 | 0.95 | 0.97 | 0.91 | 0.94 |
| 32 | 0.90 | 0.96 | 0.74 | 0.86 |
| 37 | 0.83 | 0.91 | 0.56 | 0.75 |

The results of these studies summarized in Table 4 show that the contents of the first aqueous phase solution can prevent or slow the freezing effect which was shown in Example 16 to be associated with storage of MVLs containing trilaurin as the neutral lipid at a temperature below its melting point of 46° C. The lipids used and method of manufacture were identical in both formulations; however, the encapsulated aqueous phase components were different. This suggests that the composition of the first aqueous phase may modulate either the freezing point of the triglyceride or the melting point effect, for instance by preventing the neutral lipid from transitioning to an unstable structure or markedly slowing the freezing.

The release in plasma of the tricaprin- and trilaurin-containing MVL formulations (shown in Example 16) was markedly slower than from MVL manufactured with tricaprylin, as shown in Table 4 and in later examples. It should be noted that all the plasma release assays conducted at 37° C. were initiated within 24 hours of manufacture. The storage at 2–8° C. for longer than a few days of the trilaurin, but not the tricaprin-containing formulations, resulted in morphological change in the appearance of the particles and release of encapsulated materials consistent with the "melting point effect".

EXAMPLE 17

Other Neutral Lipids

A study series was performed wherein the neutral lipids were decane, dodecane, squalene, and alpha-tocopherol to determine the scope of neutral lipids that can be used to obtain multivesicular liposomal formulations.

1. Manufacture

Multivesicular liposomes encapsulating a combination of glycine, sucrose, and Tris-EDTA were made wherein the lipid combination solution contained (per liter) 10.4 g DOPC, 2.1 g DPPG, 7.7 g cholesterol, and the triolein component (6 mol % of lipid) was replaced with either decane, dodecane, squalene, or alpha-tocopherol, (molar ratio of DOPC:DPPG:cholesterol:neutral lipid was 0.34:0.07:0.52:0.06).

The first aqueous phase solution contained 200 mM glycine, 50 mM Sucrose, 1.8 mM Tris base, and 0.5 mM EDTA, pH 7.44, with an osmolarity of 268 mOsmol. A first emulsion was made by high-speed mixing of 3 ml of lipid combination solution with 3 ml of aqueous phase solution at 9000 rpm for 9 minutes at 25–27° C. The emulsion was sheared into microdroplets (spherules) by the addition of 20 ml of a 20 mM lysine, 4% glucose solution to the mixing vessel and mixing at 4000 rpm for 1.0 min.

Examination of the spherule suspensions under the microscope indicated that the spherules prepared with each of these neutral lipids were normal in internal appearance as compared to controls prepared with triolein, tripalmitolein, or trimyristolein as the neutral lipid component.

The chloroform was removed from the microscopic droplets or spherules by transferring the suspension to a flask containing 30 ml of a 40 mM lysine, 3.2% glucose solution, placing the flask in 37° C. gyrorotary water bath, and flushing the surface of the suspension with nitrogen gas at a flow rate of 70 cfh for 20 minutes to obtain the MVL particles.

Only MVL prepared with squalene as the neutral lipid survived the solvent removal step or subsequent washing of the particles and gave rise to normal-looking MVL particles after the wash step. During the solvent removal step, decane, dodecane and alpha-tocopherol spherules began to shrink, with lobes of light-refractile material emanating from their surface. Abruptly, the particles collapsed into a crenellated structure. In some cases a pellet, albeit small as compared to controls, was recovered from the wash step, and the particles did not have the appearance of multivesicular liposome compositions.

Other Embodiments

The foregoing description of the invention is exemplary for purposes of illustration and explanation. It should be understood that various modifications can be made without departing from the spirit and scope of the invention. Accordingly, the following claims are intended to be interpreted to embrace all such modifications.

I claim:

1. A multivesicular liposome for release of a biologically active compound comprising:

a neutral lipid component having a molar ratio of a slow release neutral lipid to a fast release neutral lipid in the range from about 1:1 to 1:100, wherein the slow release neutral lipid is selected from the group consisting of triolein, tripalmitolein, trimyristolien, trilaurin, tricaprin, and mixtures thereof, and the fast release neutral lipid is selected from the group consisting of tricaprylin, tricaproin, and mixtures thereof;

an amphipathic lipid; and a biologically active compound encapsulated in water in the liposome.

2. The liposome of claim 1, wherein the melting point of the neutral lipid component is about or below 37° C.

3. The liposome of claim 1, wherein the molar ratio of the neutral lipid component to all the lipids in the liposome is in the range from about 0.01 to about 0.21.

4. The liposome of claim 1, wherein the molar ratio of the slow release neutral lipid to the fast release neutral lipid is in the range from about 1:1 to 1:27.

5. The liposome of claim 1, wherein the molar ratio of the slow release neutral lipid to the fast release neutral lipid is in the range from about 1:1 to 1:18.

6. A method for administering a biologically active compound at a desired release rate comprising administering the liposome of claim 1 to a subject in need of the biologically active compound encapsulated therein.

* * * * *

UNITED STATES PATENT AND TRADEMARK OFFICE
CERTIFICATE OF CORRECTION

PATENT NO.    : 5,962,016
DATED         : October 5, 1999
INVENTOR(S)   : Randell C. Willis It is certified that error appears in the above-identified patent and that said Letters Patent is hereby corrected as shown below:

<u>Title page,</u>
Item [56], OTHER PUBLICATIONS, please insert the following:
-- "Multivesicular Liposomes – Sustained Release of the Antimetabolite Cytarabine in the Eye", *Arch. Ophthalmol.*, Vol. 105, pp. 400-403, March, 1987" --

Signed and Sealed this

Twenty-fourth Day of June, 2003

JAMES E. ROGAN
*Director of the United States Patent and Trademark Office*